US011879015B2

(12) United States Patent
Li et al.

(10) Patent No.: US 11,879,015 B2
(45) Date of Patent: Jan. 23, 2024

(54) ANTIBODIES OR ANTIGEN-BINDING FRAGMENTS THAT BIND TO OX40

(71) Applicant: BIODURO (BEIJING) CO., LTD., Beijing (CN)

(72) Inventors: Xiang Li, Beijing (CN); Guoqian Sun, Beijing (CN); Chenguang Cai, Beijing (CN); Shiying Fu, Beijing (CN); Ting Yang, Beijing (CN); Shuang Zhao, Beijing (CN); Ying Li, Beijing (CN); Xinyue Dai, Beijing (CN); Qi Sun, Beijing (CN); Fengzhi Zhang, Beijing (CN); Youyou Lin, Beijing (CN); Yu Chen, Beijing (CN); Zhengfei Xue, Beijing (CN); Hui Pang, Beijing (CN); Ying Bai, Beijing (CN); Shin-chen Hou, Beijing (CN)

(73) Assignee: BIODURO (BEIJING) CO., LTD., Beijing (CN)

( * ) Notice: Subject to any disclaimer, the term of this patent is extended or adjusted under 35 U.S.C. 154(b) by 0 days.

(21) Appl. No.: 17/661,436

(22) Filed: Apr. 29, 2022

(65) Prior Publication Data
US 2022/0348670 A1 Nov. 3, 2022

(30) Foreign Application Priority Data

Apr. 30, 2021 (CN) .......................... 202110480042.X

(51) Int. Cl.
*C07K 16/28* (2006.01)
*A61P 35/00* (2006.01)
*A61K 39/00* (2006.01)

(52) U.S. Cl.
CPC .......... *C07K 16/2866* (2013.01); *A61P 35/00* (2018.01); *A61K 2039/505* (2013.01); *C07K 2317/34* (2013.01); *C07K 2317/565* (2013.01); *C07K 2317/76* (2013.01); *C07K 2317/92* (2013.01)

(58) Field of Classification Search
CPC .......... C07K 16/2866; C07K 2317/565; C07K 2317/569; A61P 35/00; A61K 2039/505
See application file for complete search history.

(56) References Cited

U.S. PATENT DOCUMENTS

2017/0355756 A1* 12/2017 Julien .................... A61P 25/00
2021/0269539 A1* 9/2021 Mo ..................... G01N 33/6893

FOREIGN PATENT DOCUMENTS

WO WO-2008068048 A2 * 6/2008 ............... A61P 31/10

OTHER PUBLICATIONS

Almagro JC, Fransson J. Humanization of antibodies. Front Biosci. Jan. 1, 2008;13:1619-33. (Year: 2008).*
Chen et al. Enhancement and destruction of antibody function by somatic mutation: unequal occurrence is controlled by V gene combinatorial associations.EMBO J.Jun. 15, 1995; 14(12): 2784-94. (Year: 1995).*
Kussie et al. A single engineered amino acid substitution changes antibody fine specificity.J Immunol. Jan. 1, 1994;152(1):146-52. (Year: 1994).*
Koenig et al. Mutational landscape of antibody variable domains reveals a switch modulating the interdomain conformational dynamics and antigen binding. PNAS Jan. 24, 2017 114(4)E486-E495;f irstpublished Jan. 5, 2017. (Year: 2017).*
Edwards et al. The remarkable flexibility of the human antibody repertoire;isolation of over one thousand different antibodies to a single protein,BLyS. J Mol Biol Nov. 14, 2003;334(1):103-18. (Year: 2003).*
Muyldermans S. Nanobodies: natural single-domain antibodies. Annu Rev Biochem. 2013;82:775-97. doi: 10.1146/annurev-biochem-063011-092449. Epub Mar. 13, 2013. (Year: 2013).*
Deng J et al. OX40 (CD134) and OX40 ligand, important immune checkpoints in cancer. Onco Targets Ther. Sep. 6, 2019;12:7347-7353. (Year: 2019).*
Chothia & Lesk,"Canonical Structures for the Hypervariable Regions of Immunoglobulins," J. Mol. Biol, 196:901-917 (1987).
Chothia et al., "Conformations of immunoglobulin hypervariable regions," Nature 342:877-883 (1989).
Myers and Miller, "Optimal alignments in linear space," Comput Appl Biosci (1988) vol. 4, No. 1, pp. 11-17.
Smith et al. "Comparison of Biosequences," Advances in Applied Mathematics (1981) vol. 2, pp. 482-489.
Needleman and Wunsch, "A General Method Applicable to the Search for Similarities in the Amino Acid Sequence of Two Proteins," J Mol Biol (1970) vol. 48, pp. 443-453.
Pearson and Lipman, "Improved tools for biological sequence comparison," PNAS (1988) vol. 85, pp. 2444-2448.
Karlin and Altschul, "Methods for assessing the statistical significane of molecular sequence features by using general scoring schemes," PNAS (1990) vol. 87, pp. 2264-2268.
Karlin and Altschul, "Applications and statistics for multiple high-scoring segments in the molecular sequences," PNAS (1993) vol. 90, pp. 5873-5877.
Esfahani K, Roudaia L, Buhlaiga N, et al. A review of cancer immunotherapy: from the past, to the present, to the future. Current Oncol. 2020;27(Suppl 2): S87.
Tan S, Li D, Zhu X. Cancer immunotherapy: pros, cons and beyond. Biomed Pharmacother. 2020;124: 109821.
Taefehshokr N, Baradaran B, Baghbanzadeh A, et al. Promising approaches in cancer immunotherapy. Immunobiology. 2020;225(2):151875.
Moreira RS, Bicker J, Musicco F, et al. Anti-PD-1 immunotherapy in advanced metastatic melanoma: state of the art and future challenges. Life Sci. 2020; 240: 117093.

(Continued)

*Primary Examiner* — Aurora M Fontainhas
*Assistant Examiner* — Jennifer A Benavides
(74) *Attorney, Agent, or Firm* — K&L Gates LLP

(57) ABSTRACT

The present disclosure provides antibodies that bind to OX40 and antigen binding fragments thereof, and use of the antibodies and the antigen binding fragments in the treatment of diseases for example cancers. The antibodies or the antigen binding fragments include a heavy chain variable region including one or more CDRs having an amino acid sequence selected from amino acid sequences as set forth in SEQ ID NOs: 1-12.

10 Claims, 8 Drawing Sheets

Specification includes a Sequence Listing.

(56) References Cited

OTHER PUBLICATIONS

Kwiatkowska D, Kluska P, Reich A. Beyond PD-1 immunotherapy in malignant melanoma. Dermatol Ther (Heidelb). 2019;9(2):243-257.
Wang L, Ma Q, Yao R, et al. Current status and development of anti-PD-1/PD-L1 immunotherapy for lung cancer. Int Immunopharmacol. 2020; 79:106088.
Pol J, Kroemer G. Anti-CTLA-4 immunotherapy: uncoupling toxicity and efficacy. Cell Res. 2018;28(5):501.
Rowshanravan B, Halliday N, Sansom DM. CTLA-4: a moving target in immunotherapy. Blood Journal Am Soc Hematol. 2018;131(1):58-67.
Long L, Zhang X, Chen F, et al. The promising immune checkpoint LAG-3: from tumor microenvironment to cancer immunotherapy. Genes Cancer. 2018;9(5-6): 176.
Aspeslagh S, Postel-Vinay S, Rusakiewicz S, et al. Rationale for anti-OX40 cancer immunotherapy. Eur J Cancer. 2016; 52:50-66.
Friedlaender A, Addeo A, Banna G. New emerging targets in cancer immunotherapy: the role of TIM3. ESMO Open. 2019;4(Suppl):3.
Xu Y, Wang L, Li W, et al. Killer immunoglobulin-like receptors/human leukocyte antigen class-I, a crucial immune pathway in cancer. Ann Transl Med. 2020;8(5): 244.
Solomon BL, Garrido-Laguna I. TIGIT: a novel immunotherapy target moving from bench to bedside. Cancer Immunol Immunother. 2018;67(11):1659-1667.
Ruby CE, Redmond WL, Haley D, et al. Anti-OX40 stimulation in vivo enhances CD8+ memory T cell survival and significantly increases recall responses. Eur J Immunol. 2007;37(1):157-166.
So T, Croft M. Regulation of the PKCtheta-NF-kappaB axis in T lymphocytes by the tumor necrosis factor receptor family member OX40. Front Immunol. 2012; 3:133.
Mousavi SF, Soroosh P, Takahashi T, et al. OX40 costimulatory signals potentiate the memory commitment of effector CD8+ T cells. J Immunol. 2008;181(9):5990-6001.
Massarelli E, Lam VK, Parra ER, et al. High OX-40 expression in the tumor immune infiltrate is a favorable prognostic factor of overall survival in non-small cell lung cancer. J Immunother Cancer. 2019;7(1):1-8.
Ramser M, Eichelberger S, Däster S, et al. High OX40 expression in recurrent ovarian carcinoma is indicative for response to repeated chemotherapy. BMC Cancer. 2018;18(1): 425.
Ohmura H, Yamaguchi K, Hanamura F, et al. OX40 and LAG3 are associated with better prognosis in advanced gastric cancer patients treated with anti-programmed death-1 antibody. Br J Cancer. 122(10):1507-1517.
Sawada R, Arai Y, Sagawa Y, et al. High blood levels of soluble OX40 (CD134), an immune costimulatory molecule, indicate reduced survival in patients with advanced colorectal cancer. Oncol Rep. 2019;42(5):2057-2064.
Weixler B, Cremonesi E, Sorge R, et al. OX40 expression enhances the prognostic significance of CD8 positive lymphocyte infiltration in colorectal cancer. Oncotarget. 2015;6(35): 37588.
Sarff M, Edwards D, Dhungel B, et al. OX40 (CD134) expression in sentinel lymph nodes correlates with prognostic features of primary melanomas. Am J Surg. 2008;195(5):621-625.
Chonan M, Saito R, Shoji T, et al. CD40/CD40L expression correlates with the survival of patients with glioblastomas and an augmentation in CD40 signaling enhances the efficacy of vaccinations against glioma models. Neuro Oncol. 2015;17(11): 1453-1462.
Jahan N, Talat H, Curry WT. Agonist OX40 immunotherapy improves survival in glioma-bearing mice and is complementary with vaccination with irradiated GM-CSF-expressing tumor cells. Neuro Oncol. 2018;20(1):44-54.
Guo Z, Wang X, Cheng D, et al. PD-1 blockade and OX40 triggering synergistically protects against tumor growth in a murine model of ovarian cancer. PloS One. 2014;9(2): e89350.
Kopalli SR, Kang TB, Lee KH, et al. Novel small molecule inhibitors of programmed cell death (PD)-1, and its ligand, PD-L1 in cancer immunotherapy: a review update of patent literature. Recent Pat Anticancer Drug Discov. 2019;14(2):100-112.
Kitamura, Naomi, et al. OX40 costimulation can abrogate Foxp3+ regulatory T cell-mediated suppression of antitumor immunity. International journal of cancer 125.3 2009: 630-638.
Vu, Minh Diem, et al. OX40 costimulation turns off Foxp3+ Tregs. Blood, The Journal of the American Society of Hematology 110.7 2007: 2501-2510.

\* cited by examiner

ANTIBODIES OR ANTIGEN-BINDING FRAGMENTS THAT BIND TO OX40

CROSS REFERENCE TO RELATED APPLICATIONS

This application claims the benefit of Chinese Patent Application No. 202110480042.X, filed Apr. 30, 2021. The contents of the aforementioned application are hereby incorporated by reference in its entirety.

SEQUENCE LISTING

The instant application contains a Sequence Listing which has been submitted electronically in ASCII format and is hereby incorporated by reference in its entirety. Said ASCII copy, created on Apr. 28, 2022, is named C21P8588-01US-US-SL-20220428.txt and is 9,653 bytes in size.

TECHNICAL FIELD

The present invention relates to the field of biomedicine, in particular, the present invention relates to antibodies or antigen-binding fragments that bind to OX40, nanobodies that bind to OX40, and uses thereof.

BACKGROUND ART

Immunotherapy is currently considered to be one of the main alternatives for cancer treatment[1-3]. In particular, immunotherapy reverses tumor immune escape by inhibiting or activating immune checkpoint molecules such as the PD-1/PD-L1 pathway (programmed cell death protein 1/programmed cell death 1 ligand 1)[4-6], CTLA-4 (Cytotoxic T lymphocyte antigen 4)[7,8] LAG-3 (lymphocyte activation gene 3)[9], OX40[10], TIM-3 (T cell immunoglobulin and mucin domain 3)[11], MR (killer cell immunoglobulin-like receptor)[12] and TIGIT (T cell immunoglobulin and ITIM domain)[13].

OX40, also known as CD134, TNFRSF4 or ACT35, is a membrane protein expressed in CD4+ and CD8+ T cells as well as neutrophils and NK cells, and is a member of the tumor necrosis factor receptor/tumor necrosis factor superfamily. OX40, a type I transmembrane glycoprotein with a molecular weight of about 50 kD, comprises extracellular domain having 191 amino acid residues including three intact and a slightly shorter cysteine-rich domains (CRDs). OX40 is a positive costimulatory molecule on the surface of T cells. It is not expressed on the surface of resting T cells, but is more highly expressed at 24-72 hours after T cell activation. It binds to its ligand OX40L (also known as CD252 or TNFSF4) to transmit co-stimulatory signals. OX40/OX40L signaling plays a very important role in the activation, proliferation and inhibition of apoptosis of T cells. Studies have shown that OX40 stimulates T cells to secrete a large number of cytokines and differentiate into memory and effector T cells through a variety of signaling pathways (such as the NF-κB pathway)[14-16]. In non-small cell lung cancer, ovarian cancer, advanced gastric cancer, advanced colorectal cancer, melanoma and glioblastoma, high expression of OX40 in tumor-infiltrating lymphocytes is associated with good prognosis[17-23]. Targeted agonist anti-OX40 monoclonal antibody combined with immunotherapy can improve the survival rate of mice with glioblastoma, and significantly enhance the anti-tumor immune effect of T helper cell type 1 (Th1). Combined treatment with anti-PD-1/OX40 monoclonal antibody can significantly inhibit tumor growth of ovarian cancer in mouse, enable CD8+ T cells in the spleen to produce high levels of IFN-γ and exhibit antigen-specific cytolytic activity after being stimulated by tumor antigens[24-26]. Furthermore, co-stimulation with OX40 abolishes the suppressive function of Foxp3+ Treg cells constitutively expressing OX40[10, 27-28]. It can be seen that OX40 activates effector T cells and inhibits regulatory T cells, positively regulating and stimulating tumor immunity. Based on these characteristics, the OX40 receptor is considered as one of the promising targets for novel tumor immunotherapy.

In addition to its ligand OX40L, several agonist antibodies for mediating OX40 activation have been developed, and are currently in early clinical stages. For example, pogalizumab, also known as MOXR0916 or RG7888, is a humanized effector agonist IgG1 monoclonal antibody targeting OX40, which has been clinically used in combination with atezolizumab for the treatment of advanced solid tumors. The initial results show that the combined administration exhibits good compliance[28]. In addition, agonist antibodies such as Medi0562, IBI101 and BGB-A445 have also entered into the clinical stage and are used in various types of anti-tumor therapies. Nevertheless, there is still a need to further design and develop differentiated OX40 agonist antibodies with better functions to reduce the potential risks of clinical trials.

SUMMARY OF THE INVENTION

A first aspect of the present disclosure provides an antibody and antigen-binding fragment thereof that binds to OX40, wherein the antibody or antigen-binding fragment comprises a heavy chain variable region (VH) comprising one or more DCRs having an amino acid sequence selected from amino acid sequences as shown in SEQ ID NOs: 1-12.

```
                                      (SEQ ID NO: 1)
GSIFSVYV.

(SEQ ID NO: 2)
ITPFDDNT.

(SEQ ID NO: 3)
AADWEWPEYNY.

(SEQ ID NO: 4)
GFIFSAYF.

(SEQ ID NO: 5)
INSNDDIT.

(SEQ ID NO: 6)
AAWLGAENYGY.

(SEQ ID NO: 7)
GSILDSNL.

(SEQ ID NO: 8)
INSYDDNT.

(SEQ ID NO: 9)
AAQVFVGWPYTDQMHDY.

(SEQ ID NO: 10)
GSIYDFDV.

(SEQ ID NO: 11)
INSFGDIT.

(SEQ ID NO: 12)
AADWHVLIQQVLGY
```

In some embodiments, the VH comprises CDR1, CDR2 and CDR3, wherein:

the CDR1 has the amino acid sequence as shown in SEQ ID NO: 1, 4, 7 or 10;

the CDR2 has the amino acid sequence as shown in SEQ ID NO: 2, 5, 8 or 11; and the CDR3 has the amino acid sequence as shown in SEQ ID NO: 3, 6, 9 or 12.

In some embodiments, the VH comprises:

a) CDR1, CDR2 and CDR3 having the amino acid sequences as shown in SEQ ID NOs: 1, 2 and 3, respectively;

b) CDR1, CDR2 and CDR3 having the amino acid sequences as shown in SEQ ID NOs: 4, 5 and 6, respectively;

c) CDR1, CDR2 and CDR3 having the amino acid sequences as shown in SEQ ID NOs: 7, 8 and 9, respectively; or d) CDR1, CDR2 and CDR3 having the amino acid sequences as shown in SEQ ID NO: 10, 11 and 12, respectively.

As used herein, the term "binding" or "specific binding" or its grammatical variants refer(s) to a non-random binding reaction between two molecules, such as a reaction between an antibody and the antigen to which it is directed. In certain embodiments, an antibody that specifically binds to an antigen (or an antibody that is specific for an antigen) refers to the antibody binds to the antigen with an affinity ($K_D$) less than about $10^{-5}$M, e.g., less than about $10^{-6}$ M, $10^{-7}$M, $10^{-8}$M, $10^{-9}$M, or $10^{-10}$ M or less. As used herein, "$K_D$" refers to the dissociation equilibrium constant for a particular antibody-antigen interaction, and is used to describe the binding affinity between an antibody and an antigen. The smaller the equilibrium dissociation constant, the tighter the antibody-antigen binding and the higher the affinity between the antibody and the antigen.

As used herein, the term "antibody" refers to an immunoglobulin molecule that contains at least one antigen recognition site and is capable of specifically binding to an antigen. The term "antigen" is a substance capable of inducing an immune response in the body and specifically binding to an antibody, such as protein, polypeptide, peptide, carbohydrate, polynucleotide, lipid, hapten, or a combination thereof. The binding of an antibody to an antigen is mediated by the interaction formed between them, including hydrogen bonds, van der Waals forces, ionic bonds, and hydrophobic bonds. The region on the surface of an antigen to which an antibody binds is an "antigenic determinant" or "epitope".

The term "antibody" referred to in this disclosure is to be understood in its broadest sense and includes monoclonal antibodies (including full-length monoclonal antibodies), polyclonal antibodies, antibody fragments, multispecific antibodies comprising at least two distinct antigen-binding domains (e.g., bispecific antibodies). Antibodies also include murine antibodies, humanized antibodies, chimeric antibodies, human antibodies, and antibodies of other origins. Antibodies may contain additional alterations such as unnatural amino acids, Fc effector function mutations and glycosylation site mutations. Antibodies also include post-translationally modified antibodies, fusion proteins comprising antigenic determinants of the antibody, and immunoglobulin molecules comprising any other modifications to the antigen recognition site, so long as these antibodies exhibit the desired biological activity. In other words, antibodies include immunoglobulin molecules and immunologically active fragments of immunoglobulin molecules, i.e. molecules that contain at least one antigen-binding domain.

As used herein, "variable region" (heavy chain variable region (VH) and light chain variable region (VL)) refers to the portion of the heavy and light chains that is directly involved in the binding of an antibody to an antigen. Each VH and VL region consists of three hypervariable or complementarity determining regions (CDRs) and four framework regions (FRs) arranged from N-terminal to C-terminal in the following order: FR1, CDR1, FR2, CDR2, FR3, CDR3, FR4.

As used herein, the term "CDR" refers to the complementarity determining region within antibody variable sequence. For each variable region, there are three CDRs in each variable region of the heavy and light chains, which are referred to as CDR1, CDR2, and CDR3. The exact boundaries of these CDRs are defined differently from system to system. The system described by Kabat et al (Kabat et al, Sequences of Proteins of Immunological Interest (National Institutes of Health, Bethesda, Md. (1987) and (1991)) not only provides unambiguous residue numbering system for antibody variable regions, but also provides residue boundaries that define the three CDRs. These CDRs may be referred to as Kabat CDRs. Each complementarity determining region may comprise the amino acid residues of a "complementarity determining region" defined by Kabat. Chothia et al. (Chothia & Lesk, J. Mol. Biol, 196:901-917 (1987) and Chothia et al., Nature 342:877-883 (1989)) found that certain sub-portions within the Kabat CDRs adopt nearly the same peptide backbone conformation, although there is diversity at the amino acid sequence level. These sub-portions are referred to as L1, L2 and L3 or H1, H2 and H3, respectively, where "L" and "H" represent the light and heavy chain regions, respectively. These regions may be referred to as Chothia CDRs, which have overlapping boundaries with the Kabat CDRs. There are other CDR boundary definitions that may not strictly follow one of the above systems, but will still overlap with the Kabat CDRs. The method used herein can utilize CDRs defined according to any of these systems, although preferred embodiments use CDRs defined by Kabat or Chothia.

In some embodiments, the antibody is a monovalent, bivalent or multivalent antibody.

In some embodiments, the antibody is a monospecific, bispecific or multispecific antibody.

In some embodiments, the antibody is a bispecific antibody comprising a first antigen-binding arm that binds to Ox40 and a second antigen-binding arm that binds to another antigen or another epitope on an Ox40 molecule, wherein the first antigen-binding arm comprises a heavy chain variable region (VH) as defined above.

In some embodiments, the antibody may be a murine antibody, a chimeric antibody, a humanized antibody, or a fully human antibody.

According to the amino acid sequence of the heavy chain constant region of the antibody, immunoglobulins can be divided into 5 classes (isotypes): IgA, IgD, IgE, IgG and IgM, which can be further divided into different subtypes, such as IgG1, IgG2, IgG3, IgG4, IgA1, IgA2, etc. Based on the light chain amino acid sequence, light chains can be classified as lambda chains or kappa chains. Antibodies of the present disclosure can be of any of the above classes or subclasses.

In some embodiments, the antibodies of the present disclosure are selected from the group consisting of IgG, IgA, IgM, IgE, and IgD isotypes. In some embodiments, the antibodies of the present disclosure are IgG, e.g., selected from IgG1, IgG2, IgG3, and IgG4 subtypes.

As used herein, the term "antigen-binding fragment" includes, but is not limited to: a Fab fragment having VL, CL, VH, and CH1 domains; a Fab' fragment, which is a Fab fragment with one or more cysteines residues at the C-terminal of the CH1 domain; a Fd fragment having VH and CH1 domains; a Fd' fragment having VH and CH1 domains and one or more cysteine residues at the C-terminal of the CH1 domain; a Fv fragment and scFv having VL and VH domains of a single arm of an antibody; a dAb fragment, which consists of either VH domain or VL domain; isolated CDR region(s); a F(ab')2 fragment, which is a bivalent fragment comprising two Fab' fragments connected by a disulfide bridge at the hinge region; a single-chain antibody molecule (e.g., single-chain Fv; scFv); "diabody" with two antigen-binding sites, comprising heavy chain variable region (VH) that linked to light chain variable region (VL) in the same polypeptide chain; "linear antibody" comprising a pair of tandem Fd segments (VH-CH1-VH-CH1) that together with a complementary light chain polypeptide form a pair of antigen-binding regions; and modified forms of any of the foregoing that retain antigen-binding activity.

In some embodiments of the antibody or antigen-binding fragment thereof of the present disclosure, the antigen-binding fragment is selected from the group consisting of a Fab fragment, a Fab' fragment, a F(ab')2 fragment, a Fd fragment, a Fd' fragment, a Fv fragment, a scFv fragment, a ds-scFv fragment, a dAb fragment, a single chain fragment, a diabody and a linear antibody.

A second aspect of the present disclosure provides a nanobody (also known as a single domain antibody or VHH) that binds to OX40 comprising one or more CDRs having an amino acid sequence selected from amino acid sequences as shown in SEQ ID NOs: 1-12.

In some embodiments, the nanobody comprises CDR1, CDR2 and CDR3, wherein:
the CDR1 has the amino acid sequence as shown in SEQ ID NO: 1, 4, 7 or 10;
the CDR2 has the amino acid sequence as shown in SEQ ID NO: 2, 5, 8 or 11; and
the CDR3 has the amino acid sequence as shown in SEQ ID NO: 3, 6, 9 or 12.

In some embodiments of the nanobody of the present disclosure, the nanobody comprise:
a) CDR1, CDR2 and CDR3 having the amino acid sequences as shown in SEQ ID NOs: 1, 2 and 3, respectively;
b) CDR1, CDR2 and CDR3 having the amino acid sequences as shown in SEQ ID NOs: 4, 5 and 6, respectively;
c) CDR1, CDR2 and CDR3 having the amino acid sequences as shown in SEQ ID NOs: 7, 8 and 9, respectively; or
d) CDR1, CDR2 and CDR3 having the amino acid sequences as shown in SEQ ID NO: 10, 11 and 12, respectively.

In some embodiments, the nanobody comprises a heavy chain framework region, at least a portion of which is derived from at least one of a mouse antibody, camelid antibody, human antibody, primate antibody, or mutants thereof.

In some embodiments, the nanobody has the amino acid sequence as shown in any one of SEQ ID NOs: 13-16 or the amino acid sequence with at least 80% sequence identity to any one of SEQ ID NOs: 13-16. For example, the nanobody can have the amino acid sequence with at least 85%, at least 90%, at least 95%, at least 98%, or at least 99% sequence identity to any one of SEQ ID NOs: 13-16.

```
                                            (SEQ ID NO: 13)
EVQLVESGGGLVQPGGSLRLSCAASGSIFSVYVMGWFRQAPGKGRELV

AAITPFDDNTYYPDSVEGRFTISRDNAKRMVYLQMNSLRAEDTAVYYC

AADWEWPEYNYWGQGTQVTVSS.

(SEQ ID NO: 14)
EVQLVESGGGLVQPGGSLRLSCAASGFIFSAYFMGWFRQAPGKGRELV

AAINSNDDITYYPDSVEGRFTISRDNAKRMVYLQMNSLRAEDTAVYYC

AAWLGAENYGYWGQGTQVTVSS.

(SEQ ID NO: 15)
EVQLVESGGGLVQPGGSLRLSCAASGSILDSNLMGWFRQAPGKGRELV

ASINSYDDNTYYPDSVEGRFTISRDNAKRMVYLQMNSLRAEDTAVYYC

AAQVFVGWPYTDQMHDYWGQGTQVTVSS.

(SEQ ID NO: 16)
EVQLVESGGGLVQPGGSLRLSCAASGSIYDFDVMGWFRQAPGKGRELV

AAINSFGDITYYPDSVEGRFTISRDNAKRMVYLQMNSLRAEDTAVYYC

AADWHVLIQQVLGYWGQGTQVTVSS.
```

Herein, the amino acid sequence as shown in SEQ ID NO: 13 corresponds to the nanobody called OX40 BC3-1; the amino acid sequence as shown in SEQ ID NO: 14 corresponds to the nanobody called OX40 BC3-4; the amino acid sequence as shown in SEQ ID NO: 15 corresponds to the nanobody called OX40 BC3-6; the amino acid sequence as shown in SEQ ID NO: 16 corresponds to the nanobody called OX40 BC3-7.

As understood by those skilled in the art, the relatedness between two amino acid sequences or between two nucleotide sequences can be described by the parameter "sequence identity". The percent sequence identity between two sequences can be determined, for example, by using a mathematical algorithm. Non-limiting examples of such mathematical algorithm include the Algorithm of Myers and Miller (1988) CABIOS 4:11-17, the Local Homology Algorithm of Smith et al. (1981) Adv. Appl. Math. 2:482, the Homology Alignment Algorithm of Needleman and Wunsch (1970) J. Mol. Biol. 48:443-453, the Method for Searching for Homology by Pearson and Lipman (1988) Proc. Natl. Acad. Sci. 85:2444-2448, and the Modified Form of the Algorithm of Karlin and Altschul (1990) Proc. Natl. Acad. Sci. USA 87:2264, described in the Algorithm of Karlin and Altschul (1993) Proc. Natl. Acad. Sci. USA 90:5873-5877. Sequence comparison (i.e., alignment) for determining sequence identity can be performed by using programs based on such mathematical algorithms. The programs can be appropriately executed by a computer. Examples of such programs include, but are not limited to, the CLUSTAL of the PC/Gene program, the ALIGN program (Version 2.0), and the GAP, BESTFIT, BLAST, FASTA, and TFASTA of the Wisconsin Genetics Package. Alignment using these programs can be performed, for example, by using initial parameters.

For example, the nanobody can have an amino acid sequence with one or more amino acid modifications in the amino acid sequence as shown in any one of SEQ ID NOs: 13-16. In some embodiments, the amino acid modifications do not alter the CDR sequences of the antibody, i.e., the amino acid modifications are made in the framework regions (FRs) of the variable regions.

In some embodiments, the one or more amino acid modifications refer to 1-10 amino acid modifications or 1-5 amino acid modifications, e.g., 1, 2, 3, 4, 5, 6, 7, 8, 9, or 10 amino acid modifications.

In some embodiments, the amino acid modifications are selected from substitutions, deletions, additions and/or insertions of amino acid residues. In some embodiments, the amino acid modifications are amino acid substitutions, e.g., conservative substitutions. Such conservative substitutions are preferably substitution of one amino acid residue from the following groups (a) to (e) by another amino acid residue from the same group: (a) small aliphatic, non-polar or weakly polar residues: Ala, Ser, Thr, Pro and Gly; (b) negatively charged residues and their amides: Asp, Asn, Glu and Gln; (c) positively charged residues: His, Arg and Lys; (d) large aliphatic, non-polar residues: Met, Leu, He, Val and Cys; and (e) aromatic residues: Phe, Tyr and Trp.

A third aspect of the present disclosure provides an isolated nucleic acid molecule encoding the antibody or antigen-binding fragment according to the first aspect of the disclosure or the nanobody according to the second aspect of the disclosure. In some embodiments, the nucleic acid molecule is DNA. In other embodiments, the nucleic acid molecule is RNA.

In some embodiments, the nucleic acid molecule has the nucleotide sequence as shown in any one of SEQ ID NOs: 17-20 or the nucleotide sequence with at least 80% sequence identity to any one of SEQ ID NOs: 17-20. For example, the nucleic acid molecule can have a nucleotide sequence with at least 85%, at least 90%, at least 95%, at least 98%, or at least 99% sequence identity to any one of SEQ ID NOs: 17-20.

(SEQ ID NO: 17)
GAGGTGCAGCTGGTGGAAAGCGGCGGAGGACTGGTGCAACCCGGCGGC

TCTCTGAGACTGAGCTGTGCCGCCTCCGGCTCTATCTTTAGTGTTTAT

GTTATGGGCTGGTTCAGACAAGCCCCCGGCAAGGGCAGAGAGCTGGTG

GCTGCTATTACCCCGTTTGATGATAATACCTATTACCCCGACTCCGTG

GAGGGAAGATTCACCATCTCTAGAGACAACGCCAAGAGGATGGTGTAC

CTCCAGATGAACTCTCTGAGAGCCGAGGACACAGCCGTGTATTACTGC

GCCGCTGACTGGGAATGGCCGGAATATAATTATTGGGGACAAGGCACC

CAAGTGACCGTGAGCTCC (SEQ ID NO: 18)
GAGGTGCAGCTGGTGGAAAGCGGCGGAGGACTGGTGCAACCCGGCGGC

TCTCTGAGACTGAGCTGTGCCGCCTCCGGCTTTATCTTTAGTGCTTAT

TTTATGGGCTGGTTCAGACAAGCCCCCGGCAAGGGCAGAGAGCTGGTG

GCTGCTATTAACTCGAATGATGATATTACCTATTACCCCGACTCCGTG

GAGGGAAGATTCACCATCTCTAGAGACAACGCCAAGAGGATGGTGTAC

CTCCAGATGAACTCTCTGAGAGCCGAGGACACAGCCGTGTATTACTGC

GCCGCTTGGCTGGGTGCTGAAAACTATGGCTATTGGGGACAAGGCACC

CAAGTGACCGTGAGCTCC (SEQ ID NO: 19)
GAGGTGCAGCTGGTGGAAAGCGGCGGAGGACTGGTGCAACCCGGCGGC

TCTCTGAGACTGAGCTGTGCCGCCTCCGGCAGTATCTTAGACTCTAAT

CTTATGGGCTGGTTCAGACAAGCCCCCGGCAAGGGCAGAGAGCTGGTG

GCTAGTATTAACTCGTATGATGATAATACCTATTACCCCGACTCCGTG

GAGGGAAGATTCACCATCTCTAGAGACAACGCCAAGAGGATGGTGTAC

CTCCAGATGAACTCTCTGAGAGCCGAGGACACAGCCGTGTATTACTGC

GCCGCTCAGGTTTTCGTTGGTTGGCCGTACACTGACCAGATGCATGAC

TATTGGGGACAAGGCACCCAAGTGACCGTGAGCTCC (SEQ ID NO: 20)
GAGGTGCAGCTGGTGGAAAGCGGCGGAGGACTGGTGCAACCCGGCGGC

TCTCTGAGACTGAGCTGTGCCGCCTCCGGCAGTATCTATGACTTTGAT

GTTATGGGCTGGTTCAGACAAGCCCCCGGCAAGGGCAGAGAGCTGGTG

GCTGCTATTAACTCGTTTGGCGATATTACCTATTACCCCGACTCCGTG

GAGGGAAGATTCACCATCTCTAGAGACAACGCCAAGAGGATGGTGTAC

CTCCAGATGAACTCTCTGAGAGCCGAGGACACAGCCGTGTATTACTGC

GCCGCTGACTGGCATGTTCTGATCCAGCAGGTTCTTGGTTATTGGGGA

CAAGGCACCCAAGTGACCGTGAGCTCC

The nucleic acid molecule with the nucleotide sequence as shown in SEQ ID NO: 17 encodes the nanobody with the amino acid sequence as shown in SEQ ID NO: 13. The nucleic acid molecule with the nucleotide sequence as shown in SEQ ID NO: 18 encodes the nanobody with the amino acid sequence as shown in SEQ ID NO: 14. The nucleic acid molecule with the nucleotide sequence as shown in SEQ ID NO: 19 encodes the nanobody with the amino acid sequence as shown in SEQ ID NO: 15. The nucleic acid molecule with the nucleotide sequence as shown in SEQ ID NO: 20 encodes the nanobody with the amino acid sequence as shown in SEQ ID NO: 16.

A fourth aspect of the present disclosure provides a nucleic acid construct or vector, e.g., an expression vector, comprising the nucleic acid molecule according to the third aspect of the present disclosure. In some embodiments, the vector is a eukaryotic expression vector. In other embodiments, the vector is a prokaryotic expression vector.

As used herein, "vector" refers to a nucleic acid delivery vehicle into which a polynucleotide can be inserted. When the vector can express the protein encoded by the inserted polynucleotide, the vector is called an expression vector. The vector can be introduced into a host cell by methods such as transformation, transduction, or transfection, and then the genetic material elements carried by the vector can be expressed in the host cell. Vectors are known to those skilled in the art and include, but are not limited to: (1) plasmids; (2) phagemids; (3) cosmids; (4) artificial chromosomes, such as yeast artificial chromosomes, bacterial artificial chromosomes or P1 derived artificial chromosomes; (5) phages such as lambda phage or M13 phage; and (6) animal viruses such as retrovirus, adenovirus, adeno-associated virus, herpes virus, poxvirus, baculovirus. A vector may contain various elements for controlling expression, including, but not limited to, promoter sequences, transcription initiation sequences, enhancer sequences, selection elements, and reporter genes; in addition, the vector may also contain an origin of replication.

A fifth aspect of the present disclosure provides a cell comprising the nucleic acid molecule according to the third aspect of the disclosure or the nucleic acid construct or vector, e.g., the expression vector, according to the fourth aspect of the disclosure.

A sixth aspect of the present disclosure provides an antibody conjugate comprising the OX40-binding antibody or antigen-binding fragment or nanobody of the present disclosure conjugated with an optional therapeutic agent, diagnostic agent, or imaging agent (e.g., cytotoxic molecules, radioisotopes, fluorescent labels, luminophores, chromogenic substances, or enzymes). In some embodiments, the therapeutic agent can be a cytotoxic molecule, such as a small molecule compound.

A seventh aspect of the present disclosure provides a pharmaceutical composition comprising the OX40-binding antibody or antigen-binding fragment, nanobody or antibody conjugate of the present disclosure, and a pharmaceutically acceptable carrier, excipient, or diluent.

The phrase "pharmaceutically acceptable" means those compounds, materials, compositions and/or dosage forms commensurate with a reasonable benefit/risk ratio, which, within the scope of sound medical judgment, are suitable for use in contact with human and animal tissues without excessive toxicity, irritation, allergic response or other problems or complications. As used herein, the phrase "pharmaceutically acceptable carrier, excipient and/or diluent" refer to a pharmaceutically acceptable material, composition, or vehicle such as a liquid or solid filler, diluent, excipient, solvent, medium, encapsulating material, manufacturing aid, or solvent encapsulating material, which is involved in maintaining the stability, solubility, or activity of the antibody or antigen-binding fragment thereof of the present disclosure.

The composition of the present disclosure can be formulated as a solid, liquid, or gel form for administration to a subject. For example, the composition of the present disclosure can be formulated for parenteral administration, e.g., by subcutaneous, intramuscular, intravenous or epidural injection, as e.g., a sterile solution or suspension or sustained release formulation.

In some embodiments, the composition further comprises one or more additional therapeutic agents. In some embodiments, the additional therapeutic agents include, but are not limited to, chemotherapeutic agents, growth inhibitors, cytotoxic agents, agents for radiation therapy, anti-angiogenic agents, apoptotic agents, anti-tubulin agents, and other agents for the treatment of cancers.

As used herein, the term "chemotherapeutic agent" refers to any chemical agent that has therapeutic utility in the treatment of diseases characterized by abnormal cell growth. Chemotherapeutic agents as used herein include chemical and biological agents. These agents function to inhibit the cellular activities on which cancer cells depend for continued survival. Classes of chemotherapeutic agents include alkylating/alkaloid agents, antimetabolites, hormones, or hormone analogs, and various antineobiotics.

An eighth aspect of the present disclosure provides a method of treating a cancer in a subject, comprising a step of administering to the subject an effective amount of the OX40-binding antibody or antigen-binding fragment, nanobody, antibody conjugate or pharmaceutical composition of the present disclosure.

As used herein, the term "treating" or its grammatical variants refers to therapeutic treatment whose purpose is to reverse, alleviate, ameliorate, inhibit, slow down, or cease the progression or severity of a condition associated with a disease or disorder. The term "treating" includes reducing or alleviating at least one side effect or symptom of a disease or disorder. A treatment is generally "effective" if one or more symptoms or clinical markers are reduced. Alternatively, a treatment is "effective" if the progression of the disease is reduced or ceased, that is, "treatment" includes not only the amelioration, but also the cessation, at least the slowdown of the progression or worsening of symptoms expected in the absence of the treatment. Beneficial or desired clinical outcomes include, but are not limited to, alleviation of one or more symptoms, reduction of disease severity, stabilization (i.e., not worsening) of the disease state, delay or slowdown of disease progression, amelioration or remission of the disease state, and remission (whether partial or all), whether detectable or undetectable.

As used herein, the terms "subject", "patient" and "individual" are used interchangeably herein and refer to animals, such as human. The term subject also includes "non-human mammals" such as, rats, mice, rabbits, sheep, cats, dogs, cows, pigs, and non-human primates. In preferred embodiments, the subject is a human subject.

Specific examples of the cancer include, but are not limited to: basal cell carcinoma; bile duct cancer; bladder cancer; bone cancer; breast cancer; peritoneal cancer; cervical cancer; cholangiocarcinoma; choriocarcinoma; colorectal cancer; connective tissue cancer; cancers of digestive system; endometrial cancer; esophageal cancer; eye cancer; head and neck cancer; stomach cancer; glioblastoma; liver cancer; kidney cancer; laryngeal cancer; leukemia; liver cancer; and lung cancer (e.g., small cell lung cancer, non-small cell lung cancer, lung adenocarcinoma, and lung squamous cell carcinoma); lymphomas, including Hodgkin lymphoma and non-Hodgkin lymphoma; melanoma; myeloma; neuroblastoma; oral cancer; ovarian cancer; pancreatic cancer; prostate cancer; retinoblastoma; rhabdomyosarcoma; rectal cancer; cancers of respiratory system; salivary gland cancer; sarcoma; skin cancer; squamous cell carcinoma; testicular cancer; thyroid cancer; uterine or endometrial cancer; cancers of urinary system; B-cell lymphoma; chronic lymphocytic leukemia (CLL); acute lymphoblastic leukemia (ALL); hairy cell leukemia; chronic myeloblastic leukemia, etc.

In a preferred embodiment, the cancer is selected from colorectal cancer and glioblastoma cancer.

In some embodiments of the above methods, the method further comprises a step of administering one or more additional therapies. For example, in some embodiments, the therapy is selected from chemotherapy, radiation therapy, immunotherapy, and surgical therapy.

A ninth aspect of the present disclosure provides the OX40-binding antibody or antigen-binding fragment, nanobody, antibody conjugate or pharmaceutical composition of the present disclosure for use in the treatment of a cancer in a subject. In a preferred embodiment, the cancer is selected from colorectal cancer and glioblastoma.

A tenth aspect of the present disclosure provides use of the OX40-binding antibody or antigen-binding fragment, nanobody, antibody conjugate or pharmaceutical composition of the present disclosure in the manufacture of a medicament for the treatment of a cancer in a subject. In a preferred embodiment, the cancer is selected from colorectal cancer and glioblastoma.

An eleventh aspect of the present disclosure provides a kit for detecting OX40 comprising the OX40-binding antibody or antigen-binding fragment, nanobody, or antibody conjugate of the present disclosure.

An twelfth aspect of the present disclosure provides use of the OX40-binding antibody or antigen-binding fragment, nanobody or antibody conjugate of the present disclosure in the manufacture of a kit for use in detecting OX40.

Further aspects and advantages will be described below, at least a part of which will be apparent from the following description of the accompanying drawings, and/or will be apparent to those of ordinary skill in the art from the Examples described hereinafter.

DETAILED DESCRIPTION OF THE INVENTION

Figure 1:
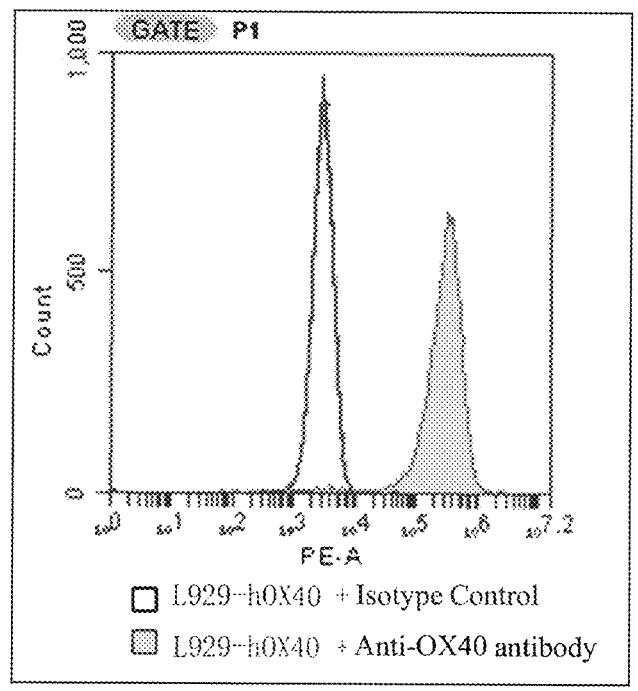
FIG. 1 is the FACS analysis result of human OX40 protein expression in the L929-hOX40 cell line.

The present invention will be further described below with specific Examples, and the advantages and characteristics of the present invention will become clearer with the description. However, these Examples are only exemplary and do not limit the scope of the present invention. It should be understood by those skilled in the art that the details and forms of the technical solutions of the present invention can be modified or replaced without departing from the spirit and scope of the present invention, while these modifications and replacements all fall within the protection scope of the present invention.

Example 1. Preparation of OX40 VHH-Fc Nanobodies 1.1. Screening of Phage Antibody Libraries (1) OX40-mFc protein (30 μg/mL dissolved in PBS, 100 μL/well) was coated on a 96-well Nunc Maxisorp immunoplate, overnight at 4° C.

(2) After blocking with 2% milk (dissolved in PBS) for 2 hours at room temperature, the immunoplate was washed with PBST for 2-4 times.

(3) About $10^{13}$ phages (dissolved in PBST containing 2% milk) were taken from each library and added to 4 coated wells, and incubated with shake at room temperature for 2 hours.

(4) The coated plate was washed 10 times with PBST, then 100 μL of 100 mM HCl was added to each well. After eluting with shake at room temperature for 5 min, the eluate was removed into an EP tube, and ⅛ volume of 1.0 M Tris-HCl (pH 11) was added for neutralization.

(5) 3 mL of competent *E. coli* SS320 in logarithmic growth phase (OD600 does not exceed 1.0) was infected with the eluted phage. After incubating at 37° C., 220 rpm for 30 min, 200 μL of the infection product was taken out and stored. M13KO7 helper phage (with final concentration to $10^{10}$/mL) was added to the remaining bacterial solution and further cultured for 1 h.

(6) The above-mentioned culture solution was transferred and seeded to 50 mL of 2YT medium (Carb$^+$, Kan$^+$), and cultured at 37° C., 220 rpm overnight.

(7) Steps (1) to (6) were repeated for the second and third rounds of screening.

(8) After three rounds of screening, the infection products of the second and third rounds were spread onto LB/Carb$^+$ plates, and cultured at 37° C. overnight.

(9) The next day, bacteria were picked to 2YT medium (Carb$^+$) containing helper phage at a concentration of $10^{10}$/mL, and cultured overnight.

(10) The binding of the phage in the monoclonal culture supernatant to OX40-mFc was identified by ELISA, and positive clones were selected for Sanger sequencing.

Through repeated screening of three batches (3 rounds of screening per batch), a total of 4 different positive clone sequences with high binding activity to OX40-mFc were obtained (see Table 1).

TABLE 1

Binding activities and sequences of antibody clones

| Clones | ELISA Results (OD450) OX40-mFc | Milk | VHH Sequences and CDR Sequences |
|---|---|---|---|
| OX40 BC3-1 | 3.452 | 0.047 | EVQLVESGGGLVQPGGSLRLSCAASGSIFSVYVMGWFRQAPGKGRELVA AITPFDDNTYYPDSVEGRFTISRDNAKRMVYLQMNSLRAEDTAVYYCAA DWEWPEYNYWGQGTQVTVSS (SEQ ID NO: 13) CDR1: GSIFSVYV (SEQ ID NO: 1) CDR2: ITPFDDNT (SEQ ID NO: 2) CDR3: AADWEWPEYNY (SEQ ID NO: 3) |

TABLE 1-continued

Binding activities and sequences of antibody clones

| Clones | ELISA Results (OD450) OX40-mFc | Milk | VHH Sequences and CDR Sequences |
|---|---|---|---|
| OX40 BC3-4 | 3.307 | 0.045 | EVQLVESGGGLVQPGGSLRLSCAASGFIFSAYFMGWFRQAPGKGRELVA AINSNDDITYYPDSVEGRFTISRDNAKRMVYLQMNSLRAEDTAVYYCAA WLGAENYGYWGQGTQVTVSS (SEQ ID NO: 14) CDR1: GFIFSAYF (SEQ ID NO: 4) CDR2: INSNDDIT (SEQ ID NO: 5) CDR3: AAWLGAENYGY (SEQ ID NO: 6) |
| OX40 BC3-6 | 3.209 | 0.045 | EVQLVESGGGLVQPGGSLRLSCAASGSILDSNLMGWFRQAPGKGRELVA SINSYDDNTYYPDSVEGRFTISRDNAKRMVYLQMNSLRAEDTAVYYCAA QVFVGWPYTDQMHDYWGQGTQVTVSS (SEQ ID NO: 15) CDR1: GSILDSNL (SEQ ID NO: 7) CDR2: INSYDDNT (SEQ ID NO: 8) CDR3: AAQVFVGWPYTDQMHDY (SEQ ID NO:9) |
| OX40 BC3-7 | 3.119 | 0.045 | EVQLVESGGGLVQPGGSLRLSCAASGSIYDFDVMGWFRQAPGKGRELVA AINSFGDITYYPDSVEGRFTISRDNAKRMVYLQMNSLRAEDTAVYYCAA DWHVLIQQVLGYWGQGTQVTVSS (SEQ ID NO: 16) CDR1: GSIYDFDV (SEQ ID NO: 10) CDR2: INSFGDIT (SEQ ID NO: 11) CDR3: AADWHVLIQQVLGY (SEQ ID NO: 12) |

1.2. Expression and Purification of VHH-Fc Antibodies

The VHH nucleotide sequences of the above four positive clones in the phage supernatant were amplified using PCR method, and fused to a CMV-12GS-FC vector with an encoding linker and human IgG FC fragment (hFC) using the In-Fusion® HD Cloning Kit (purchased from Takara). Then, the constructed plasmid was transfected to ExpiCHO cells using the matching transfection kit (purchased from Gibco) for transient protein secretion expression and enlarge culture. The cell culture solution was collected after 7 days, centrifuged at 4000 rpm for 15 min to remove components such as cell impurities. A culture supernatant containing the extracellular region of OX40 protein was obtained.

The harvested OX40 supernatant was loaded onto a Protein A affinity chromatography column (purchased from GE) with detecting the change in UV absorbance value (A280 nm), and eluted with 20 mM sodium acetate (pH3.5) to obtain the above-mentioned four humanized nanobodies targeting OX40.

Example 2. Specific Binding of OX40 VHH-Fc Antibodies to Cell Lines Expressing OX40

2.1 Construction of Stable Cell Lines Expressing OX40 Protein

The nucleotide sequence encoding the amino acid sequence of the full-length human OX40 protein (the sequence was derived from the NCBI database, the protein sequence number is NP 003318.1) was cloned into the PC MV3-Hygromycin vector to prepare a plasmid carrying human OX40 protein encoding sequence (referred to here as PCMV3-hOX40-Hygro). The above plasmid was used to transfect L929 and Jurkat cell lines, respectively. The transfected L929 and Jurkat cells were selectively cultured in DMEM+10% FBS and rpmI1640+10% FBS medium containing 500 μg/mL hygromycin, respectively, and the surviving cells were picked out one week later. Cloning was carried out in a 96-well culture plate by limiting dilution method, and some mono-clones were selected and expanded into a 24-well plate after about 2 weeks, and expanded into a 6-well plate after about 3-4 days. The expanded monoclones were screened by flow cytometry with anti-human OX40 antibody. The monoclonal cell lines with better growth and higher fluorescence intensity were selected and further expanded and cultured (the concentration of hygromycin was halved) and cryopreserved in liquid nitrogen. L929 and Jurkat stable cell lines expressing human OX40 protein were obtained, which were called L929-hOX40 and Jurkat-hOX40 stable cell lines.

Figure 2:
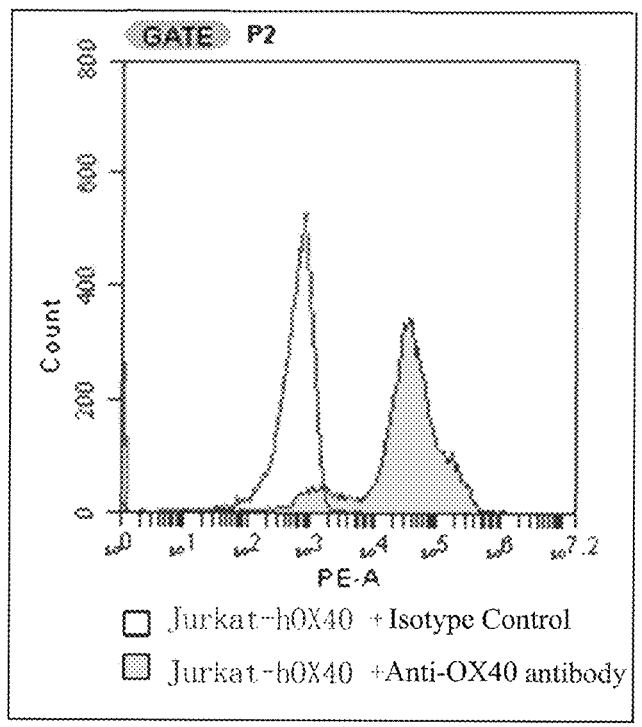
FIG. 2 is the FACS analysis result of human OX40 protein expression in the Jurkat-hOX40 cell line.

As shown in the results in FIGS. 1 and 2, the screened L929-hOX40 and Jurkat-hOX40 cell lines stably express human OX40.

2.2 FACS Detection of the Binding of Antibodies to L929-hOX40 Cells

The L929-hOX40 stable cell line constructed in Example 2.1 was cultured and expanded to 90% confluence in a cell culture flask. After washing with PBS, the cell culture was digested with 0.25% Trypsin (purchased from Thermofisher) to form a single-cell suspension, neutralized with 10% FBS-containing medium, and counted. After centrifugation at 1000 rpm for 5 min, the cells were resuspended to $2 \times 10^6$ cells/mL with FACS buffer (PBS+1% FBS), added to a 96-well FACS culture plate at 200 μL per well, centrifuged at 1000 rpm for 5 min and the supernatant was removed. A series of concentration gradients of anti-human OX40 antibodies to be tested or isotype control were added at 200 μL per well, and incubated at 4° C. for 1 hour in the dark. After centrifugation at 1000 rpm for 5 min, 200 μL of PE fluorescently labeled anti-human FC secondary antibody (purchased from Invitrogen) was added to each well, and incubated at 4° C. for 1 hour in the dark. After washing twice with FACS buffer, PBS buffer containing 1% paraformaldehyde at 200 μL per well was added to resuspend the cells, and a FACS instrument (BD Accuri C6) was used for detection and analysis.

Figure 3:
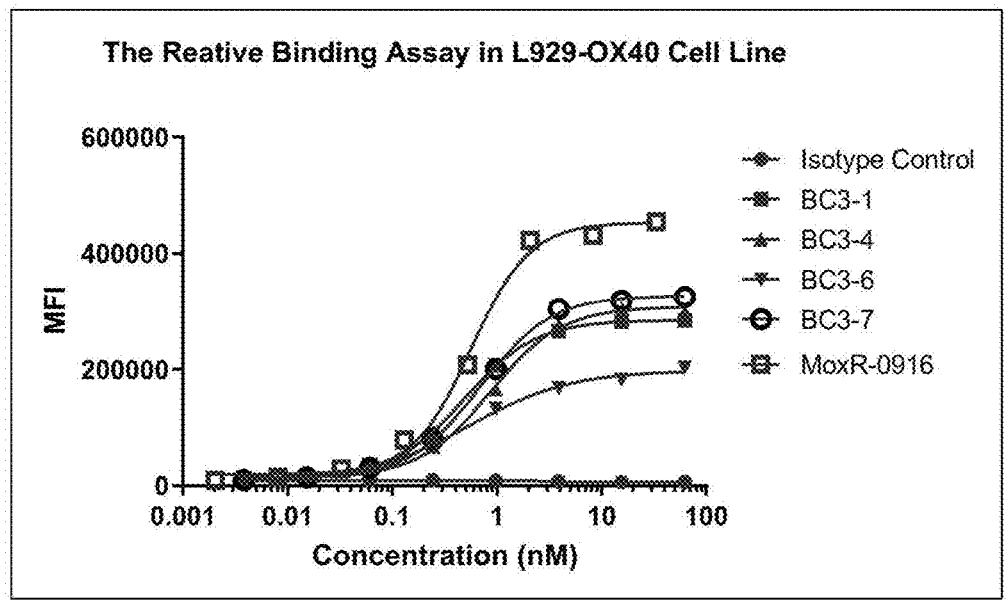
FIG. 3 is the result of FACS detecting the binding reaction of anti-OX40 nanobodies with the L929-hOX40 cell line.

The results are shown in FIG. 3, the anti-human OX40 antibodies BC3-1, BC3-4, BC3-6, and BC3-7 are all able to specifically bind to the hOX40 protein on the cell surface. The isotype control is human IgG, the positive control is MoxR-0916, and the MFI in the figure is the average fluorescence intensity value of the measured cell population. The maximum mean fluorescence intensity value and EC50 value for antibodies binding to L929-hOX40 cells are shown in Table 2.

TABLE 2

Binding of antibodies to the L929-hOX40 cell line stably expressing OX40 protein

| Antibodies | Maximum mean fluorescence intensity value (MFI) | $EC_{50}$(pM) |
|---|---|---|
| Isotype control | 8957 | / |
| BC3-1 | 284630 | 488.2 |
| BC3-4 | 307936 | 861.9 |
| BC3-6 | 198371 | 545.2 |
| BC3-7 | 327102 | 692.6 |
| MoxR-0916 | 453233 | 570.0 |

2.3 FACS Detection of the Binding of Antibodies to Jurkat-hOX40 Cells

Jurkat-hOX40 stable cell lines constructed in Example 2.1 were expanded and cultured in a cell culture flask, and cells in the logarithmic growth phase were counted. The cells were centrifuged at 1000 rpm for 5 min and then resuspended in FACS buffer (PBS+1% FBS) to $2 \times 10^6$ cells/mL, and added to a 96-well FACS culture plate at 200 μL per well. After centrifugation at 1000 rpm for 5 min, the supernatant was removed, and a series of concentration gradients of purified anti-human OX40 antibodies to be tested or isotype control were added at 200 μL per well, incubated at 4° C. for 1 hour in the dark, centrifuged at 1000 rpm for 5 min, and then added with 200 μL of PE fluorescently labeled anti-human FC secondary antibody (purchased from Invitrogen) per well, and incubated at 4° C. for 1 hour in the dark. After washing twice with FACS buffer, PBS buffer containing 1% paraformaldehyde at 200 μL per well was added to resuspend cells, and a FACS instrument (BD Accuri C6) was used for detection and analysis.

Figure 4:
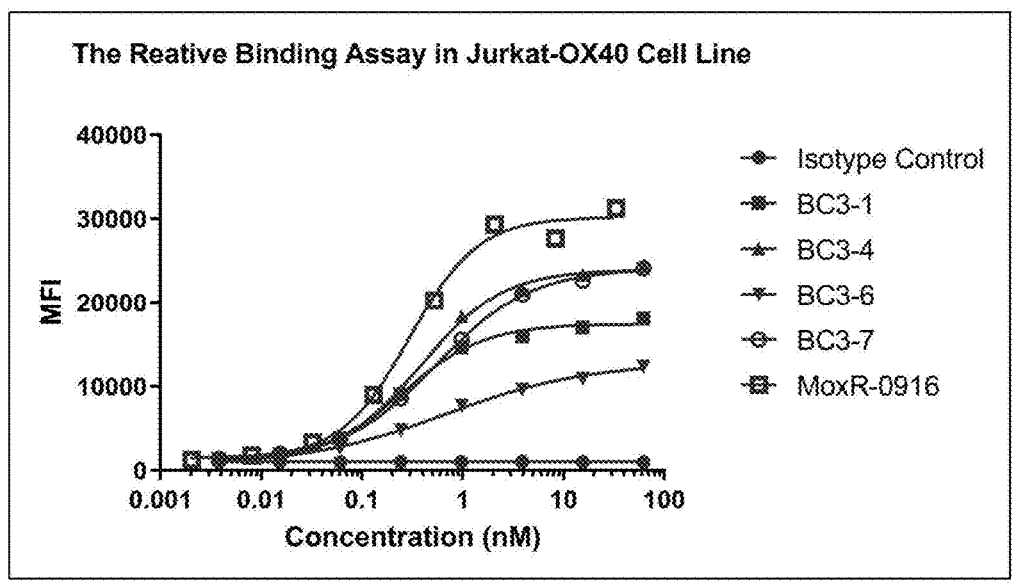
FIG. 4 is the result of FACS detecting the binding reaction of anti-OX40 nanobodies with the Jurkat-hOX40 cell line.

The results are shown in FIG. 4, the anti-human OX40 antibodies to be tested BC3-1, BC3-4, BC3-6, and BC3-7 can all specifically bind to the hOX40 protein on the cell surface. The isotype control is human IgG, the positive control is MoxR-0916, and the MFI in the figure is the average fluorescence intensity value of the measured cell population. The maximum mean fluorescence intensity value and EC50 value for antibodies binding to Jukat-hOX40 cell line are shown in Table 3.

TABLE 3

Binding of antibodies to the Kurkat-hOX40 cell line stably expressing OX40 protein

| Antibodies | Maximum mean fluorescence intensity value (MFI) | $EC_{50}$(pM) |
|---|---|---|
| Isotype control | 998.7 | / |
| BC3-1 | 17457 | 256.5 |
| BC3-4 | 23969 | 394.7 |
| BC3-6 | 12806 | 682.8 |
| BC3-7 | 24120 | 548.4 |
| MoxR-0916 | 30215 | 298.5 |

Example 3. OX40 VHH-Fc Antibody Activates NF-kB Signaling Pathway 3.1 Construction of Jurkat/NFkB-Luc-hOX40 Stable Cell Line The pGL4.32 [luc2P/NF-kB-RE/Hygro] plasmid (purchased from Promega) was transfected into Jurkat cells, cultured with RPMI1640 medium containing hygromycin and 10% FBS, and screened to obtain the Jurkat cell line, Jurkat/NF-kB-Luc, stably expressing NF-kB-RE-Luc. The OX40 lentiviral plasmid was further constructed, and the lentivirus was packaged to infect Jurkat-NF-kB-Luc cells. The infected cells were cultured with RPMI1640 medium containing hygromycin and 10% FBS, and screened to obtain the Jurkat cell line stably expressing NF-kB-RE-Luc and OX40, named Jurkat/NF-kB-Luc-hOX40.

Figure 5:
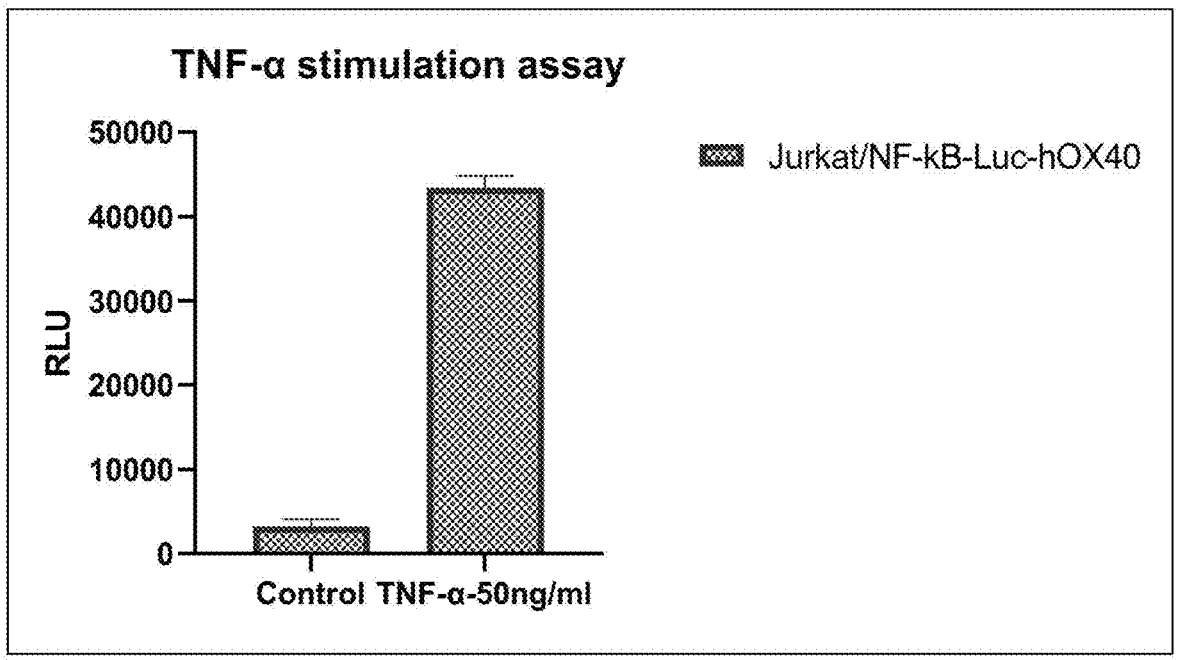
FIG. 5 is the result of NFkB RE-Luciferase expression level in the cell line stably transfected with Jurkat/NFkB-Luc-hOX40 after stimulating by PMA/Ionomycin, detected using the luciferase assay.
Figure 6:
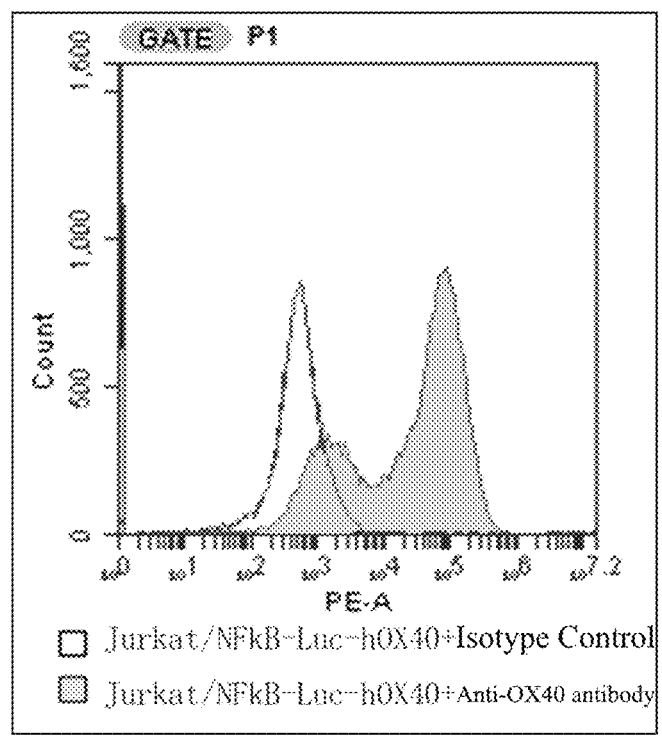
FIG. 6 is the result of FACS detecting the expression level of hOX40 in the cell line stably transfected with Jurkat/NFkB-Luc-hOX40.

FIG. 5 shows the experimental results of the NF-kB reporter gene, indicating that the screened Jurkat/NF-kB-Luc-hOX40 cell line stably expresses NF-kB-RE luciferase. FIG. 6 shows the results of the FACS assay. The results indicate that the screened Jurkat/NF-kB-Luc-hOX40 cell line stably expresses hOX40.

3.2 Construction of L929-CD32b Stable Cell Line

Figure 7:
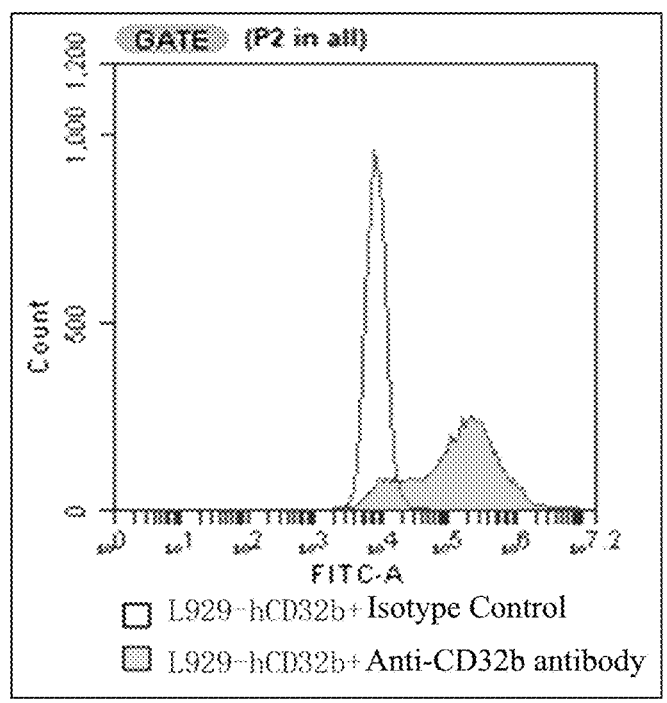
FIG. 7 is the result of FACS detecting the expression level of hCD32b in the cell line stably transfected with L929-hCD32b.

L929 cell line was transfected with a plasmid carrying the hCD32b gene. Transfected cells were selectively cultured in DMEM+10% FBS medium containing 600 μg/ml of hygromycin, and surviving cells were picked for cloning and subcloned in a 96-well culture plate by limiting dilution method. After about 2 weeks, some mono-clones were selected and expanded into a 24-well plate, and expanded into a 6-well plate after about 3-4 days. The expanded clones were screened by flow cytometry with CD32b antibody (purchased from Stemcell). FIG. 7 shows the results of FACS detection, indicating that the screened L929-hCD32b cell line stably expresses hCD32b.

3.3 NF-kB Reporter Gene Assay

The L929-hCD32b cells screened in Example 3.2 were expanded and cultured. After the cells were collected, they were resuspended in DMEM medium containing 10% FBS, and seeded in a 96-well culture plate at a density of $2 \times 10^4$/well. After overnight, the supernatant was discarded, Jurkat/NF-kB-Luc-hOX40 cells screened in Example 3.1 were added at a cell density of $5 \times 10^4$/well, and then a series of concentration gradients of anti-human OX40 antibodies to be tested or isotype control were added, and they were placed in a $CO_2$ cell incubator for continuous cultivation for 5 hours. The luciferase content was determined with the ONE-Glo Luciferase Assay System (purchased from Promega).

Figure 8:
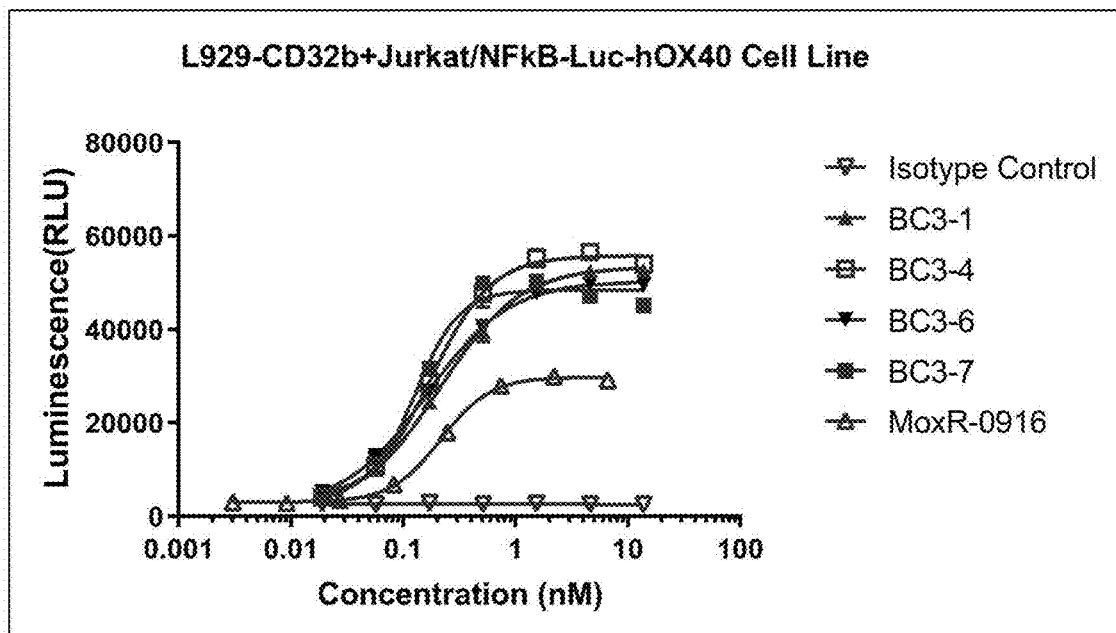
FIG. 8 is the result of the NFkB reporter gene assay detecting the activation effect of anti-OX40 nanobodies on the NFkB signaling pathway.

The results are shown in FIG. 8, in which the isotype control is human IgG, the positive control is a MoxR-0916, and RLU represents the relative luminescence signal value. The results indicate that anti-human OX40 antibodies BC3-1, BC3-4, BC3-6, and BC3-7 can significantly activate the NF-kB signaling pathway.

TABLE 4

Activation of NF-kB signaling pathway by antibodies

| Antibodies | Maximum value (RLU) | $EC_{50}$(pM) |
|---|---|---|
| Isotype control | 2650 | / |
| BC3-1 | 53365 | 209.2 |
| BC3-4 | 55747 | 175.1 |
| BC3-6 | 50273 | 162.4 |
| BC3-7 | 48390 | 129.8 |
| MoxR-0916 | 29821 | 216.9 |

Figure 9:
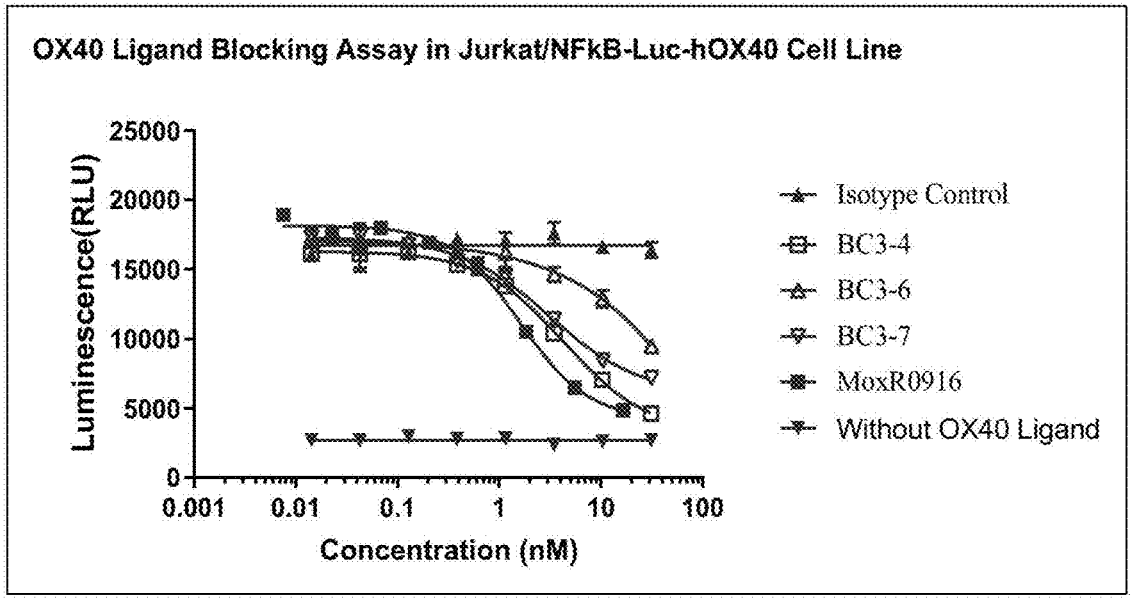
FIG. 9 is the result of the competitive binding between the anti-OX40 nanobodies and hOX40L to human OX40 protein in the cell line stably transfected with Jurkat/NFkB-Luc-hOX40, detected using the NFkB reporter gene assay.

Example 4. Inhibitory Effect of Anti-Human OX40 Antibodies on the Binding of OX40 to OX40L Protein 4.1 Inhibitory Effect of Anti-Human OX40 Antibodies on the Binding of OX40 to OX40L Protein Detected by Reporter Gene Assay The Jurkat/NF-kB-Luc-hOX40 cells constructed in Example 3.1 were added to a 96-well cell culture plate at a cell density of $5 \times 10^4$/well. OX40L protein diluted to a concentration of 0.3 µg/ml and a series of serial dilutions of anti-human OX40 antibodies or isotype control were added simultaneously to the cells, and luciferase assay was performed after 5 hours of incubation in a $CO_2$ incubator. The results are shown in FIG. 9. The results show that the anti-human OX40 antibodies BC3-1, BC3-4, BC3-6, and BC3-7 can inhibit the binding of OX40L to OX40, indicating that these antibodies compete with OX40L for the epitope in OX40.

4.2 Inhibitory Effect of Anti-Human OX40 Antibodies on the Binding of OX40 to OX40L Protein Detected by FACS The L929-hOX40 stable cell line constructed in Example 2.1 was cultured and expanded to 90% confluence in a cell culture flask. The cells were washed with PBS, digested with 0.25% Trypsin (purchased from Thermofisher) to form a single-cell suspension, neutralized with a medium containing 10% FBS, and then were counted. The cells were centrifuged at 1000 rpm for 5 min and resuspended to $2 \times 10^6$ cells/mL with FACS buffer (PBS+1% FBS), added to a 96-well FACS culture plate at 200 µL per well, centrifuged at 1000 rpm for 5 min, and then the supernatant was discarded. 0.5 µg/ml of anti-human OX40 antibodies or isotype control and a series of serial dilutions of OX40L protein were added, and incubated at 4° C. for 1 hour in the dark. After centrifugation at 1000 rpm for 5 min, 200 µL of PE fluorescently labeled anti-human FC secondary antibody (purchased from Invitrogen) was added to each well, and incubated at 4° C. for 1 hour in the dark. The cells were washed twice with FACS buffer, and 200 µL of PBS buffer containing 1% paraformaldehyde was added to each well to resuspend the cells, and a FACS instrument (BD Accuri C6) was used for detection and analysis.

Figure 10:
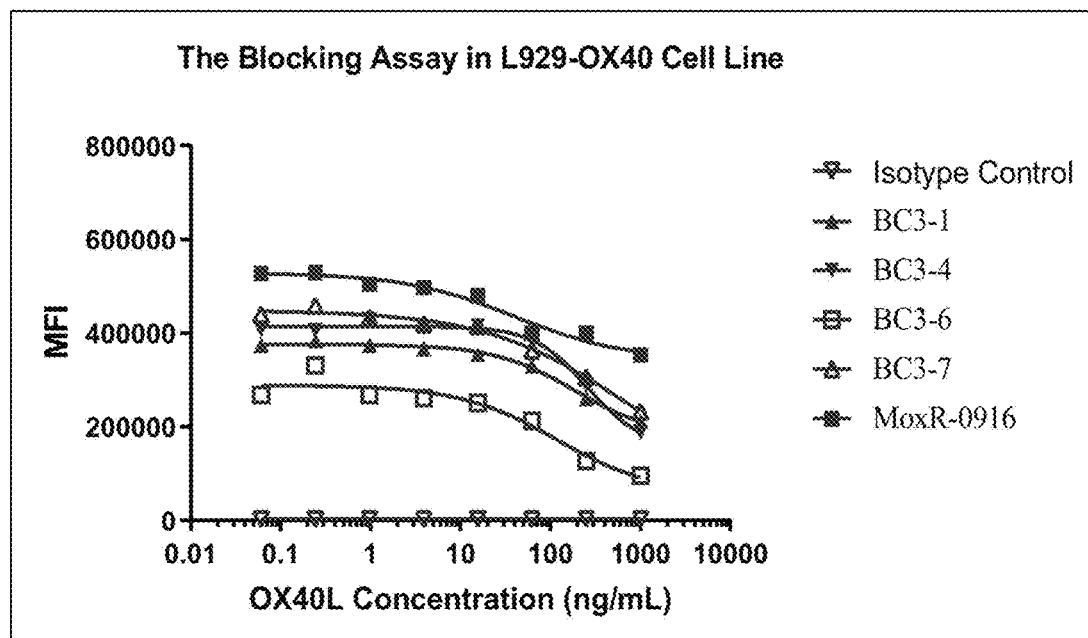
FIG. 10 is the result of FACS detecting the competitive binding between the OX40 nanobodies and hOX40L to human OX40 protein in the L929-OX40 cell line.

The results are shown in FIG. 10. The results indicate that the anti-human OX40 antibodies BC3-1, BC3-4, BC3-6, and BC3-7 compete with OX40L for binding to OX40, further indicating that these antibodies compete with OX40L for the epitope in OX40.

Example 5. Binding of Anti-Human OX40 Antibodies to OX40 on the Surface of T Cells 5.1 The cryopreserved PBMC cells (purchased from AllCells) were revived in RPMI 1640 medium containing 10% FBS at a seeding density of $0.5 \times 10^6$ cells/ml, added with 2 µg/ml of PHA and 2 µg/ml of IL-2, incubated in an incubator for 48 hours, and then the cells were collected. The cells were centrifuged at 1000 rpm for 5 min and then resuspended to $2 \times 10^6$ cells/mL in FACS buffer (PBS+1% FBS), and added to a 96-well FACS culture plate at 200 µL per well. After centrifugation at 1000 rpm for 5 minutes, the supernatant was discarded. APC fluorescently labeled anti-human OX40 antibody (purchased from Biolegend) was added in a volume of 5 uL per well. The expression level of OX40 on the surface of T cells was detected after the T cells in PBMC were activated by PHA.

Figure 11:
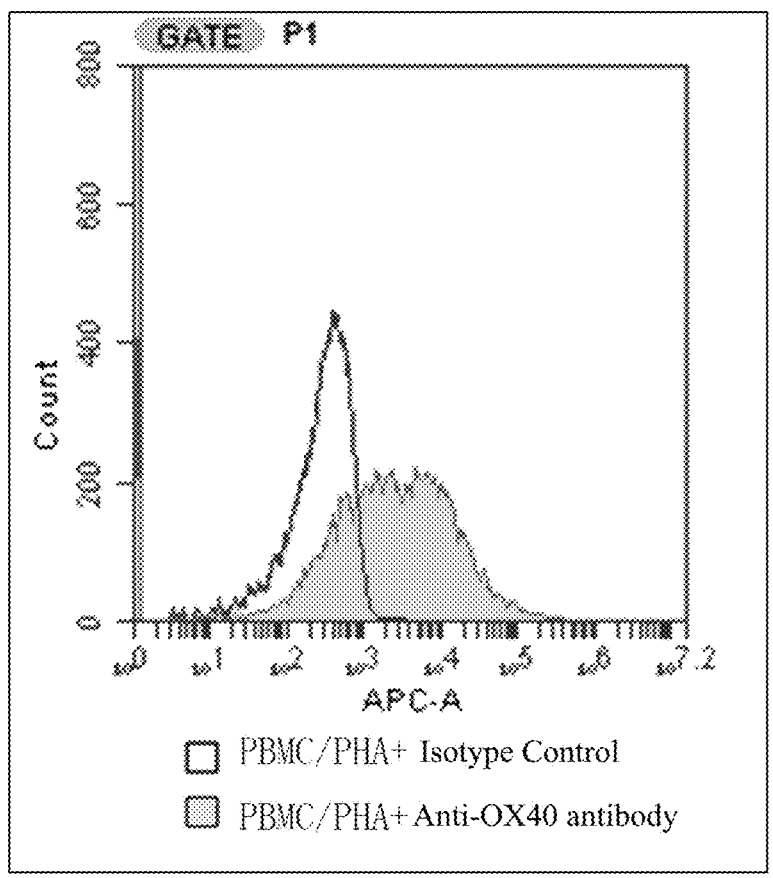
FIG. 11 is the result of FACS detecting the expression level of OX40 on the surface of T cells after activation by PHA.

The results are shown in FIG. 11, indicateing that the resting T cells do not express OX40, while activated T cells, upon activation by PHA, express high levels of OX40.

5.2 The cryopreserved PBMC cells (purchased from AllCells) were revived in RPMI 1640 medium containing 10% FBS at a seeding density of $0.5 \times 10^6$ cells/ml, added with 2 µg/ml of PHA and 2 µg/ml of IL-2, incubated in an incubator for 48 hours, and then the cells were collected. The cells were centrifuged at 1000 rpm for 5 min and then resuspended to $3 \times 10^6$ cells/mL with FACS buffer (PBS+1% FBS), and added to a 96-well FACS culture plate at 200 µL per well. After centrifugation at 1000 rpm for 5 min, the supernatant was discarded. A series of serial dilutions of anti-OX40 antibodies were added, and incubated at 4° C. for 1 hour in the dark. After centrifugation at 1000 rpm for 5 min, 200 µL of PE fluorescently labeled anti-human FC secondary antibody (purchased from Invitrogen) was added to per well, and incubated at 4° C. for 1 hour in the dark. After washing twice with FACS buffer, 200 µL of PBS containing 1% paraformaldehyde was added to each well to resuspend the cells, and a FACS instrument (BD Accuri C6) was used for detection and analysis.

Figure 12:
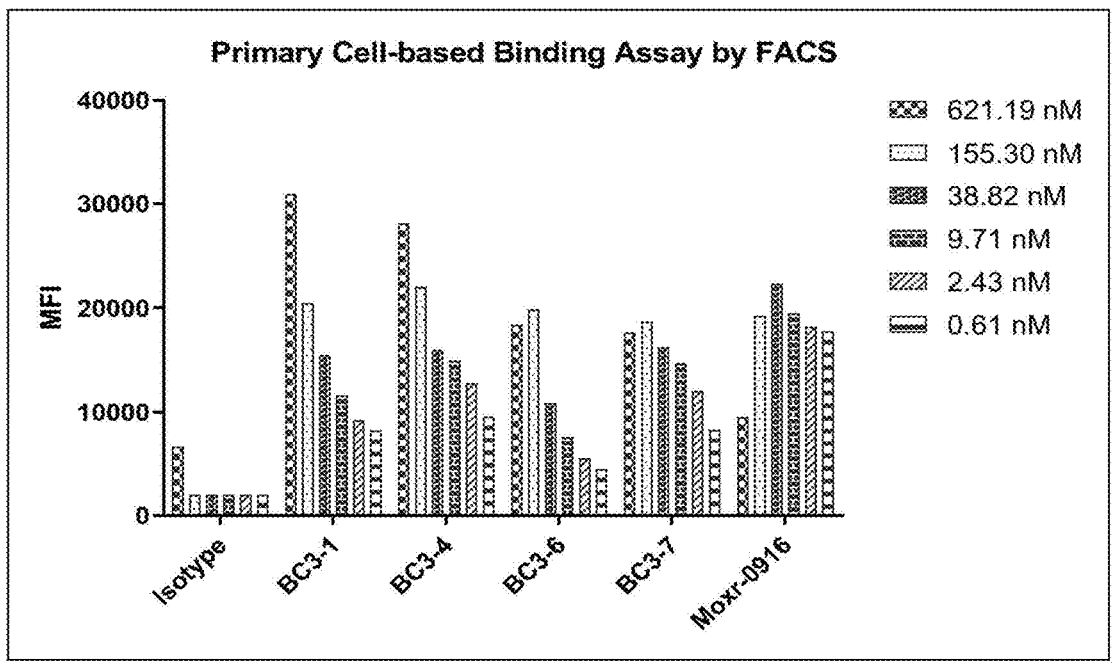
FIG. 12 is the result of FACS detecting the binding reaction of anti-OX40 nanobodies with hOX40 on the surface of T cells, based on the PBMC activation experiment.

The results are shown in FIG. 12. The MFI in the figure is the average fluorescence intensity value of the measured cell population. The results indicate that the anti-human OX40 antibodies BC3-1, BC3-4, BC3-6, and BC3-7 can specifically bind to the hOX40 protein on the surface of activated T cells in a concentration-dependent manner.

Example 6. Epitope Identification of Anti-Human OX40 Antibodies 6.1 Construction of Plasmids Expressing Different Domains of Human OX40

Using the PCMV3 plasmid as the backbone, a truncated expression vector of OX40 (humanized) that lacks the CRD1 domain was constructed, and named PCMV3-SP-OX40 (CRD2-3-4) (human); a chimeric expression vector with deletion of human CRD1 and CRD2, with replacement of human CRD3 by murine CRD3, and containing human CRD4 domain was constructed, and named PCMV3-SP-OX40 (CRD3mus-CRD4human); a murine full-length OX40 expression vector was constructed and named PCMV3-OX40 (Mus); a human full-length OX40 expression vector was constructed and named PCMV3-OX40 (human).

Figure 13:
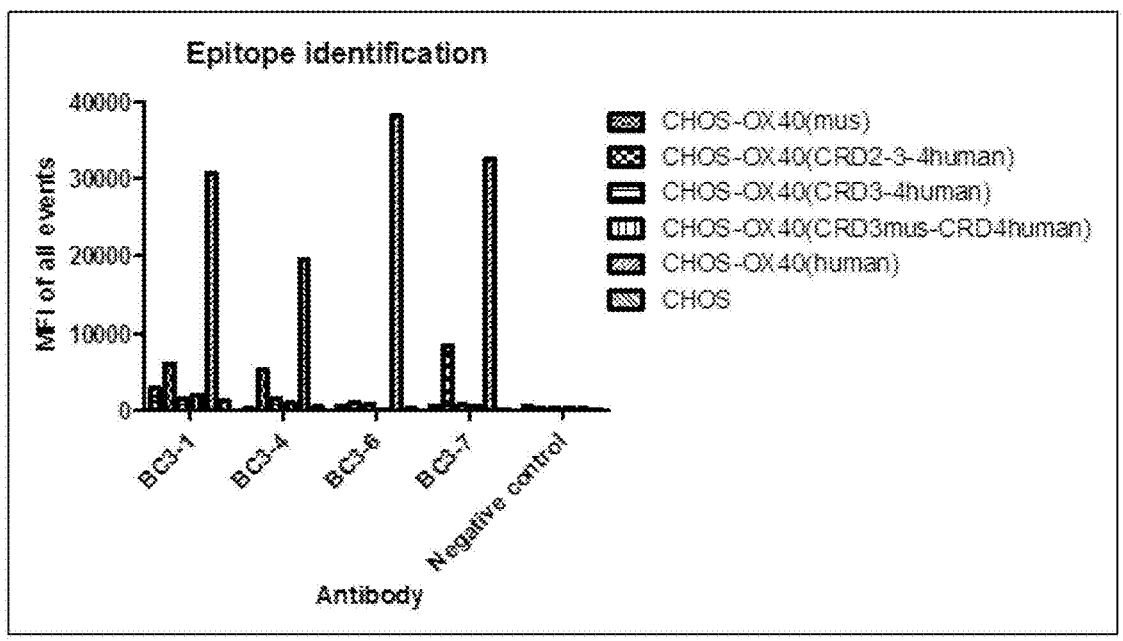
FIG. 13 is the result of FACS detecting the binding of anti-OX40 nanobodies to CHO-S cells transiently transfected to express different epitopes of human OX40.

6.2 Identification of Antigenic Epitope Targeted by Anti-Human OX40 Antibodies by FACS Transient transfection of OX40 expression vector: CHO-S cells were revived, and passaged for at least 2 times, and then seeded into a 6-well plate at a density of $1 \times 10^6$ cells/well. At the following day, the above expression vectors expressing different domains of OX40 were transfected into CHO-S cells by PEI transfection method. At 24 h after transfection, anti-human OX40 antibodies BC3-1, BC3-4, BC3-6, and BC3-7 were incubated with the transfected cells, and the binding of the antibodies to the cells was detected by FACS. As shown in the results in FIG. 13, anti-human OX40 antibodies BC3-1, BC3-4, BC3-6, and BC3-7 bind to CHOS-OX40 (CRD2-3-4human) and CHOS-OX40 (human), while do not bind to CHOS, CHOS-OX40 (mus), CHOS-OX40 (CRD3-4human) and CHOS-OX40 (CRD3mus-CRD4human). The above results indicate that the antigenic epitope of BC3-1, BC3-4, BC3-6, and BC3-7 to OX40 is located in CRD2.

The contents of all references (including literature references, published patents, published patent applications, and co-pending patent applications) cited throughout this application are expressly incorporated herein by reference in their entirety. Unless otherwise defined, all technical and scientific terms used herein have the same meaning as commonly known to those of ordinary skill in the art.

According to the above description, one skilled in the art can easily ascertain the essential characteristics of this invention, and without departing from the spirit and scope of the invention, can make various changes and modifications of the invention to adapt it to various uses and conditions. Accordingly, other Examples are within the scope of the appended claims.

REFERENCES

1. Esfahani K, Roudaia L, Buhlaiga N, et al. A review of cancer immunotherapy: from the past, to the present, to the future. Current Oncol. 2020; 27(Suppl 2): S87.
2. Tan S, Li D, Zhu X. Cancer immunotherapy: pros, cons and beyond. Biomed Pharmacother. 2020; 124: 109821.
3. Taefehshokr N, Baradaran B, Baghbanzadeh A, et al. Promising approaches in cancer immunotherapy. Immunobiology. 2020; 225(2):151875.
4. Moreira RS, Bicker J, Musicco F, et al. Anti-PD-1 immunotherapy in advanced metastatic melanoma: state of the art and future challenges. Life Sci. 2020; 240: 117093.
5. Kwiatkowska D, Kluska P, Reich A. Beyond PD-1 immunotherapy in malignant melanoma. Dermatol Ther (Heidelb). 2019; 9(2):243-257.
6. Wang L, Ma Q, Yao R, et al. Current status and development of anti-PD-1/PD-L1 immunotherapy for lung cancer. Int Immunopharmacol. 2020; 79:106088.
7. Pol J, Kroemer G. Anti-CTLA-4 immunotherapy: uncoupling toxicity and efficacy. Cell Res. 2018; 28(5):501.
8. Rowshanravan B, Halliday N, Sansom D M. CTLA-4: a moving target in immunotherapy. Blood Journal Am Soc Hematol. 2018; 131(1):58-67. [Google Scholar]
9. Long L, Zhang X, Chen F, et al. The promising immune checkpoint LAG-3: from tumor microenvironment to cancer immunotherapy. Genes Cancer. 2018; 9(5-6): 176.
10. Aspeslagh S, Postel-Vinay S, Rusakiewicz S, et al. Rationale for anti-OX40 cancer immunotherapy. Eur J Cancer. 2016; 52:50-66.
11. Friedlaender A, Addeo A, Banna G. New emerging targets in cancer immunotherapy: the role of TIM3. ESMO Open. 2019; 4(Suppl):3. [Google Scholar]
12. Xu Y, Wang L, Li W, et al. Killer immunoglobulin-like receptors/human leukocyte antigen class-I, a crucial immune pathway in cancer. Ann Transl Med. 2020; 8(5): 244.
13. Solomon B L, Garrido-LagunaI. TIGIT: a novel immunotherapy target moving from bench to bedside. Cancer Immunol Immunother. 2018; 67(11):1659-1667.
14. Ruby C E, Redmond W L, Haley D, et al. Anti-OX40 stimulation in vivo enhances CD8+ memory T cell survival and significantly increases recall responses. Eur J Immunol. 2007; 37(1):157-166.
15. So T, Croft M. Regulation of the PKCθ-NF-κB axis in T lymphocytes by the tumor necrosis factor receptor family member OX40. Front Immunol. 2012; 3:133.
16. Mousavi S F, Soroosh P, Takahashi T, et al. OX40 costimulatory signals potentiate the memory commitment of effector CD8+ T cells. J Immunol. 2008; 181(9):5990-6001.
17. Massarelli E, Lam V K, Parra E R, et al. High OX-40 expression in the tumor immune infiltrate is a favorable prognostic factor of overall survival in non-small cell lung cancer. J Immunother Cancer. 2019; 7(1):1-8.
18. Ramser M, Eichelberger S, Däster S, et al. High OX40 expression in recurrent ovarian carcinoma is indicative for response to repeated chemotherapy. BMC Cancer. 2018; 18(1): 425.
19. Ohmura H, Yamaguchi K, Hanamura F, et al. OX40 and LAG3 are associated with better prognosis in advanced gastric cancer patients treated with anti-programmed death-1 antibody. Br J Cancer. 122(10):1507-1517.
20. Sawada R, Arai Y, Sagawa Y, et al. High blood levels of soluble OX40 (CD134), an immune costimulatory molecule, indicate reduced survival in patients with advanced colorectal cancer. Oncol Rep. 2019; 42(5):2057-2064.
21. Weixler B, Cremonesi E, Sorge R, et al. OX40 expression enhances the prognostic significance of CD8 positive lymphocyte infiltration in colorectal cancer. Oncotarget. 2015; 6(35): 37588.
22. Sarff M, Edwards D, Dhungel B, et al. OX40 (CD134) expression in sentinel lymph nodes correlates with prognostic features of primary melanomas. Am J Surg. 2008; 195(5):621-625.
23. Chonan M, Saito R, Shoji T, et al. CD40/CD40L expression correlates with the survival of patients with glioblastomas and an augmentation in CD40 signaling enhances the efficacy of vaccinations against glioma models. Neuro Oncol. 2015; 17(11): 1453-1462.
24. Jahan N, Talat H, Curry W T. Agonist OX40 immunotherapy improves survival in glioma-bearing mice and is complementary with vaccination with irradiated GM-CSF-expressing tumor cells. Neuro Oncol. 2018; 20(1): 44-54.
25. Guo Z, Wang X, Cheng D, et al. PD-1 blockade and OX40 triggering synergistically protects against tumor growth in a murine model of ovarian cancer. PloS One. 2014; 9(2): e89350. [Crossref], [Web of Science®], [Google Scholar]
26. Kopalli S R, Kang T B, Lee K H, et al. Novel small molecule inhibitors of programmed cell death (PD)-1, and its ligand, PD-L1 in cancer immunotherapy: a review update of patent literature. Recent Pat Anticancer Drug Discov. 2019; 14(2):100-112
27. Kitamura, Naomi, et al. OX40 costimulation can abrogate Foxp3+ regulatory T cell-mediated suppression of antitumor immunity. International journal of cancer 125.3 2009: 630-638.
28. Vu, Minh Diem, et al. OX40 costimulation turns off Foxp3+ Tregs. Blood, The Journal of the American Society of Hematology 110.7 2007: 2501-2510.

The invention claimed is:

1. A nanobody that binds to OX40, comprising:
   a) a CDR1, a CDR2 and a CDR3 having the amino acid sequences as shown in SEQ ID NOs: 1, 2 and 3, respectively;
   b) a CDR1, a CDR2 and a CDR3 having the amino acid sequences as shown in SEQ ID NOs: 4, 5 and 6, respectively;
   c) a CDR1, a CDR2 and a CDR3 having the amino acid sequences as shown in SEQ ID NOs: 7, 8 and 9, respectively; or
   d) a CDR1, a CDR2 and a CDR3 having the amino acid sequences as shown in SEQ ID NOs: 10, 11 and 12, respectively.

2. The nanobody of claim 1, wherein the nanobody comprises a heavy chain framework region, at least a portion of which is derived from at least one of a mouse antibody, camelid antibody, human antibody, primate antibody, or mutants thereof.

3. The nanobody of claim 2, wherein the nanobody comprises the amino acid sequence as shown in any one of SEQ ID NOs: 13-16, or an amino acid sequence with at least 80% sequence identity to any one of SEQ ID NOs: 13-16.

4. The nanobody of claim 2, wherein the nanobody comprises the amino acid sequence as shown in any one of SEQ ID NOs: 13-16.

5. An antibody conjugate comprising the nanobody of claim 1 conjugated to a therapeutic agent, a diagnostic agent, or an imaging agent.

6. A pharmaceutical composition comprising the nanobody of claim 1 and a pharmaceutically acceptable carrier, excipient or diluent.

7. A kit for detecting OX40, comprising the nanobody of claim 1.

8. An isolated nucleic acid molecule encoding the nanobody of claim 1.

9. The nucleic acid molecule of claim 8, wherein the nucleic acid molecule comprises the nucleotide sequence as shown in any one of SEQ ID NOs: 17-20.

10. A method of treating a cancer in a subject, comprising a step of administering to the subject an effective amount of the nanobody of claim 5, wherein the cancer is a colorectal cancer or a glioblastoma.

\* \* \* \* \*

SEQUENCE LISTING

<160> NUMBER OF SEQ ID NOS: 20

<210> SEQ ID NO 1
<211> LENGTH: 8
<212> TYPE: PRT

```
<213> ORGANISM: Artificial sequence
<220> FEATURE:
<223> OTHER INFORMATION: VH CDR1

<400> SEQUENCE: 1

Gly Ser Ile Phe Ser Val Tyr Val
1               5

<210> SEQ ID NO 2
<211> LENGTH: 8
<212> TYPE: PRT
<213> ORGANISM: Artificial sequence
<220> FEATURE:
<223> OTHER INFORMATION: VH CDR2

<400> SEQUENCE: 2

Ile Thr Pro Phe Asp Asp Asn Thr
1               5

<210> SEQ ID NO 3
<211> LENGTH: 11
<212> TYPE: PRT
<213> ORGANISM: Artificial sequence
<220> FEATURE:
<223> OTHER INFORMATION: VH CDR3

<400> SEQUENCE: 3

Ala Ala Asp Trp Glu Trp Pro Glu Tyr Asn Tyr
1               5                   10

<210> SEQ ID NO 4
<211> LENGTH: 8
<212> TYPE: PRT
<213> ORGANISM: Artificial sequence
<220> FEATURE:
<223> OTHER INFORMATION: VH CDR1

<400> SEQUENCE: 4

Gly Phe Ile Phe Ser Ala Tyr Phe
1               5

<210> SEQ ID NO 5
<211> LENGTH: 8
<212> TYPE: PRT
<213> ORGANISM: Artificial sequence
<220> FEATURE:
<223> OTHER INFORMATION: VH CDR2

<400> SEQUENCE: 5

Ile Asn Ser Asn Asp Asp Ile Thr
1               5

<210> SEQ ID NO 6
<211> LENGTH: 11
<212> TYPE: PRT
<213> ORGANISM: Artificial sequence
<220> FEATURE:
<223> OTHER INFORMATION: VH CDR3

<400> SEQUENCE: 6

Ala Ala Trp Leu Gly Ala Glu Asn Tyr Gly Tyr
1               5                   10

<210> SEQ ID NO 7
<211> LENGTH: 8
<212> TYPE: PRT
<213> ORGANISM: Artificial sequence
```

```
<220> FEATURE:
<223> OTHER INFORMATION: VH CDR1

<400> SEQUENCE: 7

Gly Ser Ile Leu Asp Ser Asn Leu
1               5

<210> SEQ ID NO 8
<211> LENGTH: 8
<212> TYPE: PRT
<213> ORGANISM: Artificial sequence
<220> FEATURE:
<223> OTHER INFORMATION: VH CDR2

<400> SEQUENCE: 8

Ile Asn Ser Tyr Asp Asp Asn Thr
1               5

<210> SEQ ID NO 9
<211> LENGTH: 17
<212> TYPE: PRT
<213> ORGANISM: Artificial sequence
<220> FEATURE:
<223> OTHER INFORMATION: VH CDR3

<400> SEQUENCE: 9

Ala Ala Gln Val Phe Val Gly Trp Pro Tyr Thr Asp Gln Met His Asp
1               5                   10                  15

Tyr

<210> SEQ ID NO 10
<211> LENGTH: 8
<212> TYPE: PRT
<213> ORGANISM: Artificial sequence
<220> FEATURE:
<223> OTHER INFORMATION: VH CDR1

<400> SEQUENCE: 10

Gly Ser Ile Tyr Asp Phe Asp Val
1               5

<210> SEQ ID NO 11
<211> LENGTH: 8
<212> TYPE: PRT
<213> ORGANISM: Artificial sequence
<220> FEATURE:
<223> OTHER INFORMATION: VH CDR2

<400> SEQUENCE: 11

Ile Asn Ser Phe Gly Asp Ile Thr
1               5

<210> SEQ ID NO 12
<211> LENGTH: 14
<212> TYPE: PRT
<213> ORGANISM: Artificial sequence
<220> FEATURE:
<223> OTHER INFORMATION: VH CDR3

<400> SEQUENCE: 12

Ala Ala Asp Trp His Val Leu Ile Gln Gln Val Leu Gly Tyr
1               5                   10

<210> SEQ ID NO 13
<211> LENGTH: 118
<212> TYPE: PRT
```

```
<213> ORGANISM: Artificial sequence
<220> FEATURE:
<223> OTHER INFORMATION: Amino acid sequence of nanobody

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Val Tyr
            20                  25                  30

Val Met Gly Trp Phe Arg Gln Ala Pro Gly Lys Gly Arg Glu Leu Val
        35                  40                  45

Ala Ala Ile Thr Pro Phe Asp Asp Asn Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Asp Trp Glu Trp Pro Glu Tyr Asn Tyr Trp Gly Gln Gly Thr
            100                 105                 110

Gln Val Thr Val Ser Ser
        115

<210> SEQ ID NO 14
<211> LENGTH: 118
<212> TYPE: PRT
<213> ORGANISM: Artificial sequence
<220> FEATURE:
<223> OTHER INFORMATION: Amino acid sequence of nanobody

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ala Tyr
            20                  25                  30

Phe Met Gly Trp Phe Arg Gln Ala Pro Gly Lys Gly Arg Glu Leu Val
        35                  40                  45

Ala Ala Ile Asn Ser Asn Asp Asp Ile Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Trp Leu Gly Ala Glu Asn Tyr Gly Tyr Trp Gly Gln Gly Thr
            100                 105                 110

Gln Val Thr Val Ser Ser
        115

<210> SEQ ID NO 15
<211> LENGTH: 124
<212> TYPE: PRT
<213> ORGANISM: Artificial sequence
<220> FEATURE:
<223> OTHER INFORMATION: Amino acid sequence of nanobody

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Leu Asp Ser Asn
            20                  25                  30
```

```
Leu Met Gly Trp Phe Arg Gln Ala Pro Gly Lys Gly Arg Glu Leu Val
        35                  40                  45

Ala Ser Ile Asn Ser Tyr Asp Asn Thr Tyr Tyr Pro Asp Ser Val
 50                  55                  60

Glu Gly Arg Phe Thr Ile Ser Arg Asp Asn Ala Lys Arg Met Val Tyr
 65                  70                  75                  80

Leu Gln Met Asn Ser Leu Arg Ala Glu Asp Thr Ala Val Tyr Tyr Cys
                 85                  90                  95

Ala Ala Gln Val Phe Val Gly Trp Pro Tyr Thr Asp Gln Met His Asp
            100                 105                 110

Tyr Trp Gly Gln Gly Thr Gln Val Thr Val Ser Ser
            115                 120
```

```
<210> SEQ ID NO 16
<211> LENGTH: 121
<212> TYPE: PRT
<213> ORGANISM: Artificial sequence
<220> FEATURE:
<223> OTHER INFORMATION: Amino acid sequence of nanobody

<400> SEQUENCE: 16

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Tyr Asp Phe Asp
            20                  25                  30

Val Met Gly Trp Phe Arg Gln Ala Pro Gly Lys Gly Arg Glu Leu Val
        35                  40                  45

Ala Ala Ile Asn Ser Phe Gly Asp Ile Thr Tyr Tyr Pro Asp Ser Val
 50                  55                  60

Glu Gly Arg Phe Thr Ile Ser Arg Asp Asn Ala Lys Arg Met Val Tyr
 65                  70                  75                  80

Leu Gln Met Asn Ser Leu Arg Ala Glu Asp Thr Ala Val Tyr Tyr Cys
                 85                  90                  95

Ala Ala Asp Trp His Val Leu Ile Gln Gln Val Leu Gly Tyr Trp Gly
            100                 105                 110

Gln Gly Thr Gln Val Thr Val Ser Ser
            115                 120
```

```
<210> SEQ ID NO 17
<211> LENGTH: 354
<212> TYPE: DNA
<213> ORGANISM: Artificial sequence
<220> FEATURE:
<223> OTHER INFORMATION: Nucleotide sequence of nanobody

<400> SEQUENCE: 17
gaggtgcagc tggtggaaag cggcggagga ctggtgcaac ccggcggctc tctgagactg      60
agctgtgccg cctccggctc tatctttagt gtttatgtta tgggctggtt cagacaagcc     120
cccggcaagg gcagagagct ggtggctgct attaccccgt ttgatgataa taccattac     180 cccgactccg tggagggaag attcaccatc tctagagaca cgccaagag gatggtgtac     240 ctccagatga actctctgag agccgaggac acagccgtgt attactgcgc cgctgactgg     300
gaatggccgg aatataatta ttggggacaa ggcacccaag tgaccgtgag ctcc           354
```

```
<210> SEQ ID NO 18
<211> LENGTH: 354
<212> TYPE: DNA
```

<210> SEQ ID NO 19
<211> LENGTH: 372
<212> TYPE: DNA
<213> ORGANISM: Artificial sequence
<220> FEATURE:
<223> OTHER INFORMATION: Nucleotide sequence of nanobody

<400> SEQUENCE: 18

```
gaggtgcagc tggtggaaag cggcggagga ctggtgcaac ccggcggctc tctgagactg      60
agctgtgccg cctccggctt tatctttagt gcttatttta tgggctggtt cagacaagcc     120
cccggcaagg gcagagagct ggtggctgct attaactcga atgatgatat tacctattac     180
cccgactccg tggagggaag attcaccatc tctagagaca acgccaagag gatggtgtac     240
ctccagatga actctctgag agccgaggac acagccgtgt attactgcgc cgcttggctg     300
ggtgctgaaa actatggcta ttggggacaa ggcacccaag tgaccgtgag ctcc           354
```

<210> SEQ ID NO 19
<211> LENGTH: 372
<212> TYPE: DNA
<213> ORGANISM: Artificial sequence
<220> FEATURE:
<223> OTHER INFORMATION: Nucleotide sequence of nanobody

<400> SEQUENCE: 19

```
gaggtgcagc tggtggaaag cggcggagga ctggtgcaac ccggcggctc tctgagactg      60
agctgtgccg cctccggcag tatcttagac tctaatctta tgggctggtt cagacaagcc     120
cccggcaagg gcagagagct ggtggctagt attaactcgt atgatgataa tacctattac     180
cccgactccg tggagggaag attcaccatc tctagagaca acgccaagag gatggtgtac     240
ctccagatga actctctgag agccgaggac acagccgtgt attactgcgc cgctcaggtt     300
ttcgttggtt ggccgtacac tgaccagatg catgactatt ggggacaagg cacccaagtg     360
accgtgagct cc                                                         372
```

<210> SEQ ID NO 20
<211> LENGTH: 363
<212> TYPE: DNA
<213> ORGANISM: Artificial sequence
<220> FEATURE:
<223> OTHER INFORMATION: Nucleotide sequence of nanobody

<400> SEQUENCE: 20

```
gaggtgcagc tggtggaaag cggcggagga ctggtgcaac ccggcggctc tctgagactg      60
agctgtgccg cctccggcag tatctatgac tttgatgtta tgggctggtt cagacaagcc     120
cccggcaagg gcagagagct ggtggctgct attaactcgt ttggcgatat tacctattac     180
cccgactccg tggagggaag attcaccatc tctagagaca acgccaagag gatggtgtac     240
ctccagatga actctctgag agccgaggac acagccgtgt attactgcgc cgctgactgg     300
catgttctga tccagcaggt tcttggttat tggggacaag gcacccaagt gaccgtgagc     360
tcc                                                                   363
```